US007807866B2

(12) United States Patent
Ghulam Kadir

(10) Patent No.: US 7,807,866 B2
(45) Date of Patent: Oct. 5, 2010

(54) METHOD AND COMPOSITIONS FOR THE PRODUCTION OF TRANSGENIC PLANTS

(75) Inventor: Ahmad Parveez Ghulam Kadir, Selangor (MY)

(73) Assignee: Malaysian Palm Oil Board, Kajang, Selangor (MY)

( * ) Notice: Subject to any disclaimer, the term of this patent is extended or adjusted under 35 U.S.C. 154(b) by 501 days.

(21) Appl. No.: 10/178,919

(22) Filed: Jun. 25, 2002

(65) Prior Publication Data
US 2003/0159175 A1    Aug. 21, 2003

(30) Foreign Application Priority Data
Aug. 13, 2001    (MY)    .............................. PI 20013795

(51) Int. Cl.
    C12N 15/82    (2006.01)
    A01H 5/00    (2006.01)
(52) U.S. Cl. ........................ 800/278; 800/281; 800/293; 800/294
(58) Field of Classification Search ................. 800/295, 800/278, 293, 294, 288, 298; 536/23.1; 435/320, 435/468, 469, 470
See application file for complete search history.

(56) References Cited

U.S. PATENT DOCUMENTS

| | | | | |
|---|---|---|---|---|
| 5,510,255 A * | 4/1996 | Knauf et al. | ................ | 435/91.3 |
| 6,028,248 A * | 2/2000 | Somerville et al. | ........... | 800/281 |
| 6,040,498 A * | 3/2000 | Stomp et al. | ................. | 800/294 |
| 6,288,304 B1 * | 9/2001 | Moloney et al. | ............ | 800/288 |
| 6,448,476 B1 * | 9/2002 | Barry | ......................... | 800/300 |
| 6,459,017 B1 * | 10/2002 | Jeknic et al. | ................ | 800/278 |

OTHER PUBLICATIONS

Parveez et al. Journal of Oil Palm Research. 1998. 10(2), p. 29-38.*
Parveez et al. Industrial Crops and Products. 1997. 6(1), p. 41-50.*
Paranjothy et al, 1989, Current Status and Strategies of Oil Palm Tissue Culture Research Palm Oil Research Institute of Malaysia, in the 1989 PORIM International Palm Oil Development Conference; Module II Agriculture Proceedings, pp. 109-221.*
Kadir et al, Dec. 2000, Biochemical Society Transactions 28(6): 969-972.*
Kadir et al 1998, Industrial Crops and Products 8:17-27.*
Dodds and Roberts 1982, in Experiments in Plant Tissue Culture, Cambridge University Press, pp. 2, 28-29 and 47.*
Arencibia, A., et al. "Production of transgenic sugarcane (*Saccharium officinarum* L.) plants by intact cell electroporation," Plant Cell Rep. 14:305-309, 1995.
Barcelo, P. et al., "Transgenic cereal (*Tritordeum*) plants obtained at high frequency by microprojectile bombardment of inflorescence tissue," The Plant Journal 5:583-592, 1994.
Barker, R.F. et al., "Nucleotide sequence of the T-DNA region from the *Agrobacterium tumefaciens* octopine Ti plasmid pTi15955," Plant Molecular Biology, 2:335-350, 1983.

Bechtold, N. et al., "*In planta Agrobacterium* mediated gene transfer by infiltration of adult *Arabidopsis thaliana* plants," C.R. Acad. Sci. Paris 316:1194-1199, 1993.
Bevan, M.W., et al., "A chimaeric antibiotic resistance gene as a selectable marker for plant cell transformation," Nature 304:184-187, 1983.
Bower R. et al., "Transgenic sugarcane plants via microprojectile bombardment," The Plant Journal 2(3):409-416, 1992.
Bytebier B., et al., "T-DNA organization in tumor cultures and transgenic plants of the monocotyledon *Asparagus officinalis*," Proc. Natl. Acad. Sci. USA 84:5345-5349, 1987.
Casas A.M., et al., "Cereal Transformation Through Particle Bombardment," Plant Breeding Reviews 13:235-264, 1995.
Castillo, A.M., et al., Rapid Production of Fertile Transgenic Plants of Rye (*Secale cereale* L.), Bio/Technology 12:1366-1371, 1994.
Chee, P.P. et al., "Using Polymerase Chain Reaction to Identify Transgenic Plants," Plant Molecular Biology Manual C3:1-28, 1991.
Christensen, A.H. et al., "Ubiquitin Promoter-based Vectors for High-Level Expression of Selectable and/or Screenable Marker Genes in Monocotyledonous Plants," Transgenic Research 5:213-218, 1996.
Christou, P. et al., "Production of Transgenic Rice (*Oryza sativa* L.) Plants From Agronomically Important Indica and Japonica Varieties Via Electric Discharge Particle Acceleration of Exogenous DNA Into Immature Zygotic Embryos," Biotechnology 9:957-962, 1991.
Datta, S.K. et al., "Genetically Engineered Fertile Indica-Rice Recovered From Protoplasts," Biotechnology 8:736-740, 1990.
DeBlock M. et al., "Engineering Herbicide Resistance in Plants by Expression of a Detoxifying Enzyme," The EMBO Journal 6(9):2513-2518, 1987.
De Cleene, M. et al., "The Host Range of Crown Gall," The Botanical Review 42(4):389-466, 1976.
De Greve, H. et al., "Nucleotide Sequence and Transcript Map of the *Agrobacterium tumefaciens* Ti Plasmid-Encoded Octopine Synthase Gene," Journal of Molecular and Applied Genetics 1(6):499-511, 1982.
Dellaporta, S.L., et al., "Molecular Cloning of the Maze R-*nj* Allele by Transposon Tagging With AC," Chromosome Structure and Function, 263-282, 1988.
D'Halluin, K. et al., "Transgenic Maize Plants by Tissue Electroporation," The Plant Cell 4:1495-1505, 1992.

(Continued)

Primary Examiner—David H Kruse
(74) Attorney, Agent, or Firm—Morgan Lewis & Bockius LLP

(57) ABSTRACT

The present invention relates generally to a process of producing transgenic plants and more particularly transgenic oil palm plants carrying exogenous genetic material which confers on said plants or cells of said plants particular phenotypic traits. The present invention further provides plant parts, reproductive material and plant products from the transgenic plants. The present invention particularly provides transgenic plants and even more particularly transgenic oil palm plants having beneficial and useful phenotypic characteristics not present at least to the same extent in non-transgenic plants of the same species. The present invention is further directed to oil, and particularly palm oil, having beneficial and desirable characteristics, produced by the transgenic plants made in accordance with the present invention.

62 Claims, 12 Drawing Sheets
(12 of 12 Drawing Sheet(s) Filed in Color)

OTHER PUBLICATIONS

Eeuwens, C.J. et al., "Mineral Requirements for Growth and Callus Initiation of Tissue Explants Excised from Mature Coconut Palms (*Cocos nuficera*) and Cultured in vitro," Physiol. Plant 36(23):23-28, 1976.

Ellis, T.H.N., "Approaches to the Genetic Mapping of Pea," Modern Methods of Plant Analysis 16:117-160, 1993.

Feinberg, A.P. et al., "A Technique for Radiolabeling DNA Restriction Endonuclease Fragments to High Specific Activity," Analytical Biochemistry 137:266-267, 1984.

Fraley. R.T. et al., "Expression of Bacterial Genes in Plant Cells," Proc. Natl. Acad. Sci. USA 80:4803-4807, 1983.

Frame, B.R. et al., "Production of Fertile Transgenic Maize Plants by Silicon Carbide Whisker-Mediated Transformation," The Plant Journal 6(6):941-948, 1994.

Fromm, M.E. et al., "Inheritance and Expression of Chimeric Genes in the Progeny of Transgenic Maize Plants," Biotechnology 8:833-838, 1990.

Garfinkel, D.J. et al., "Genetic Analysis of Crown Gall: Fine Structure Map of the T-DNA by Site-Directed Mutagenesis," Cell 27:143-153, 1981.

Guo, Y. et al., "Laser-mediated gene transfer in rice," Physiologia Plantarum 93:19-24, 1995.

Hinchee, M.A.W. et al., "Production of Transgenic Soybean Plants Using *Agtrobacterium*-Mediated DNA Transfer," Biotechnology 6:915-922, 1988.

Hoekema, A. et al., "A binary plant vector strategy based on separation of *vir*- and T-region of the *Agrobacterium tumefaciens* Ti-plasmid," Nature 303:179-180, 1983.

Hood, E.E. et al., "The Hypervirulence of *Agrobacterium tumefaciens* A281 Is Encoded in a Region of pTiBo542 Outside of T-DNA," Journal of Bacteriology 168(3):1291-1301, 1986.

Horn, M.E. et al., "Transgenic Plants of Orchardgrass (*Dactylis glomerata* L.) from protoplasts," Plant Cell Reports 7:469-472. 1988.

Horsch, R.B. et al., "A Simple and General Method for Transferring Genes into Plants," Science 227:1229-1231, 1985.

Ikuta, N. et al., "The α-Amylase Gene As a Marker for Gene Cloning: Direct Screening of Recombinant Clones," Biotechnology 8:241-242, 1990.

Ishida, Y. et al., "High efficiency transformation of maize (*Zey mays* L.) mediated by *Agrobacterium tumefaciens*," Nature Biotechnology 14:745-750, 1996.

Jähne, A. et al., "Regeneration of transgenic, microspore-derived, fertile barley," Theor. Appl. Genet. 89:525-533, 1994.

Jähne, A. et al., "Genetic engineering of cereal crop plants: a review," Euphytica 85:35-44, 1995.

Janssen, B-J et al., "Localized transient expression of GUS in leaf discs following cocultivation with *Agrobacterium*, "Plant Molecular Biology 14:61-72, 1989.

Jefferson, R.A.,"Assaying Chimeric Genes in Plants: The GUS Gene Fusion System," Plant Molecular Biology Reporter 5(4):387-405, 1987.

Kaeppler, H.F. et al., "Silicon carbide fiber-mediated DNA delivery into plant cells," Plant Cell Reports 9:415-418, 1990.

Katz, E. et al., "Cloning and Expression of the Tyrosinase Gene from *Streptomyces* antibioticus in *Streptomyces* lividans," Journal of General Microbiology 129:2703-2714, 1983.

Klein, T.M. et al., "High-velocity microprojectiles for delivering nucleic acids into living cells," Nature 327:70-73, 1987.

Klein, T.M. et al., "Stable genetic transformation of intact *Nicotiana* cells by the particle bombardment process," Proc. Natl. Acad. Sci. USA 85:8502-8505, 1988.

Klöti, A. et al., "Gene transfer by electroporation into intact scutellum cells of wheat embryos," Plant Cell Reports 12:671-675, 1993.

Koncz, C. et al., "The promoter of $T_L$-DNA gene 5 controls the tissue-specific expression of chimaeric genes carried by a novel type of *Agrobacterium* binary vector," Mol. Gen. Genet. 204:383-396, 1986.

Kuehnle, A.R. et al., "Transformation of *Dendrobium* orchid using particle bombardment of protocorms," Plant Cell Reports 11:484-488, 1992.

Laursen, C.M. et al., "Production of fertile transgenic maize by electroporation of suspension culture cells," Plant Molecular Biology 24:51-61, 1994.

Lazo, G.R. et al., "A DNA Transformation-Competent *Arabidopsis* Genomic Library in *Agrobacterium*," Biotechnology 9:963-967, 1991.

Lörz, H. et al., "Gene transfer to cereal cells mediated by protoplast transformation," Mol. Gen. Genet 199:178-182, 1985.

Lowe, K. et al., "Germline Transformation of Maize Following Manipulation of Chimeric Shoot Meristems," Biotechnology 13:677-682, 1995.

May, G.D. et al., "Generation of Transgenic Banana (*Musa acuminata*) Plants via *Agrobacterium*-Mediated Transformation," Biotechnology 13:486-492, 1995.

Murashige, T. et al., "A Revised Medium for Rapid Growth and Bio Assays with Tobacco Cultures," Physiologia Plantarum 15:473-497, 1962.

Niedz, R.P. et al., "Green fluorescent protein: an in vivo reporter of plant gene expression," Plant. Cell Reports 14:403-406, 1995.

Ow, D.W. et al., "Transient and Stable Expression of the Firefly Luciferase Gene in Plant Cells and Transgenic Plants," Science 234:856-859, 1986.

Paranjothy, K.O. et al., "Current Status and Strategies of Oil Palm Tissue Culture Research," Palm Oil Research Institute of Malaysia, pp. 109-221, 1989.

Potrykus, I., "Gene Transfer to Cereals: An Assessment," Biotechnology 8:535-542, 1990.

Potrykus, I. et al., "Direct gene transfer to cells of a graminaceous monocot," Mol. Gen. Genet 199:183-188, 1985.

Prasher, D. et al, "Cloning and Expression of the cDNA Coding for Aequorin, A Bioluminescent Calcium-Binding Protein," 126(3):1259-1268, 1985.

Rajanaidu, N. et al., "World-wide Performance of DXP Planting Materials and Future Prospects," Palm Oil Research Institute of Malaysia pp. 1-29, 1995.

Rashid, H. et al., "Transgenic plant production mediated by *Agrobacterium* in *Indica* rice," Plant Cell Reports 15:727-730, 1996.

Rhodes, C.A. et al., "Genetically Transformed Maize Plants from Protoplasts," Science 240:204-207, 1988.

Salomon, F. et al., "Genetic identification of functions of TR-DNA transcripts in octopine crown galls," EMBO Journal :141-146, 1984.

Sambrook, J. et al., "Molecular Cloning," A Laboratory Manual $2^{nd}$ Ed. pp. 1.33-1.39, and 9.31-9.58, 1989.

Schnorf, M. et al., "An improved approach for transformation of plant cells by microinjection: molecular and genetic analysis," Transgenic Research 1:23-30, 1991.

Shimamoto, K. et al., "Fertile transgenic rice plants regenerated from transformed protoplasts," Nature 338:274-276, 1989.

Southern, E.M., "Detection of Specific Sequences Among DNA Fragments Separated by Gel Electrophoresis," J. Mol. Biol. 98:503-517, 1975.

Stalker, D.M. et al., "Herbicide Resistance in Transgenic Plants Expressing a Bacterial Detoxification Gene," Science 242:419-423, 1988.

Sutcliffe, J.G. et al., "Nucleotide sequence of the ampicillin resistance gene of *Escherichia coli* plasmid pBR322,"Proc. Natl. Acad. Sci. USA 75(8):3737-3741, 1978.

Tarmizi, A.H. et al., "Establishment of Oil Palm Embryogenic Suspension Cultures from Calli Derived from Various Sources," $11^{th}$ National Biotechnology Seminar, pp. 22-24, 1999.

Thillet, J. et al., "Site-directed Mutagenesis of Mouse Dihydrofolate Reductase," The Journal of Biological Chemistry 263(25):12500-12508, 1988.

Töpfer, R. et al., "Uptake and Transient Expression of Chimeric Genes in Seed-Derived Embryos," The Plant Cell, 1:133-139, 1989.

Vasil, V. et al., "Herbicide Resistant Fertile Transgenic Wheat Plants Obtained by Microprojectile Bombardment of Regenerable Embryogenic Callus," Biotechnology 10:667-674, 1992.

Wang, Z. et al., "Transgenic Plants of Tall Fescue (*Festuca arundinacea* Schred.) Obtained by Direct Gene Transfer to Protoplasts," Biotechnology 10:691-696, 1992.

Weber, G. et al., "Uptake of DNA in chloroplasts of *Brassica napus* (L.) facilitated by a UV-laser microbeam," European Journal of Cell Biology 49:73-79, 1989.

Weber, G. et al., "Genetic changes induced in higher plant cells by a laser microbeam," Physiologia Plantarum 79:190-193, 1990.

Xiayi, K. et al., "Electroporation of immature maize zygotic embryos and regeneration of transgenic plants," Transgenic Research 5:219-221, 1996.

Xu, X. et al., "Fertile transgenic Indica rice plants obtained by electroporation of the seed embryo cells," Plant Cell Reports 13:237-242, 1994.

Zambryski, P. et al., "Ti plasmid vector for the introduction of DNA into plant cells without alteration of their normal regeneration capacity," The EMBO Journal 2(12):2143-2150, 1983.

Zukowki, M.M. et al., "Chromogenic identification of genetic regulatory signals in *Bacillus subtilis* based on expression of a cloned *Pseudomonas* gene," Proc. Natl. Acad. Sci. USA 80:1101-1105, 1983.

* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
ggtctgcacc atcgtcaacc                                                  20

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
actcaccgcg acgtctgtcg                                                  20
```

METHOD AND COMPOSITIONS FOR THE PRODUCTION OF TRANSGENIC PLANTS

FIELD OF THE INVENTION

The present invention relates generally to a process of producing transgenic plants and more particularly transgenic oil palm plants carrying exogenous genetic material which confers on said plants or cells of said plants particular phenotypic traits. The present invention further provides plant parts, reproductive material and plant products from the transgenic plants. The present invention particularly provides transgenic plants and even more particularly transgenic oil plants having beneficial and useful phenotypic characteristics not present at least to the same extent in non-transgenic plants of the same species. The present invention is further directed to oil, and particularly palm oil, having beneficial and desirable characteristics, produced by the transgenic plants made in accordance with the present invention.

BACKGROUND OF THE INVENTION

Reference to any prior art in this specification is not, and should not be taken as, an acknowledgement or any form of suggestion that this prior art forms part of the common general knowledge in Malaysia, Australia or any other country.

Bibliographic details of the publications referred to by author in this specification are collected at the end of the description.

The demand for oil and fats is expected to increase dramatically with the increase in world population. Oil palm (*Elaeis guineensis* and *Elaeis oleifera*), which produces the palm oil and palm kernel oil, is the highest yielding oil crop in the world and was forecasted to contribute around a quarter of the world's oil and fats demand by the year 2020 (Rajanaidu and Jalani, 1995). Due to the demand, there is a need to increase the quality and yield of palm oil and palm kernel oil and to rapidly develop new characteristics when required.

Current methods of improvement via conventional breeding are very slow due to the nature of the breeding process and the very long generation time for oil palm plants. Genetic engineering offers a means of manipulating the characteristics of plants. However, until the advent of the present invention, protocols for its use in oil palm plants were not well developed.

Genetic engineering is a specialized method of improving plant quality by introducing foreign genes into the whole plant by genetic transformation. Genetic engineering processes are often unique to particular plants. An efficient tissue culture system is required in order to produce complete chimeric-free transgenic plants after successful delivery and integration of foreign genes into cells that are able to regenerate into a whole plant. To engineer any plant genetically, it is important to obtain a transgenic plant that possesses the gene(s) in the whole plant. The gene(s) need to be expressed in the whole plant if the objective is, for example, to develop disease or herbicide resistant plants. On the other hand, if the interest is in improving or modifying a specific trait in a particular tissue such as in fruit, tissue specific promoters are desirable. In both situations, the presence of chimeric plants is undesirable.

The genetic transformation process involves the uptake of a foreign gene by competent cells, its integration into the chromosome and subsequently the expression of the genes product. The process starts with the penetration of a gene into a cell through the cell wall. Various methods are available for plant gene transfer and are basically divided into two main groups; namely *Agrobacterium*-mediated gene transfer and direct gene transfer. Discussion on some of the various plant transformation methods available is provided below. However, none of the methodologies has been successful in producing chimeric-free transgenic oil palm plants.

*Agrobacterium*-Mediated Transformation

*Agrobacterium tumafaciens* is capable of introducing foreign genes into plant cells via a tumor-inducing plasmid known as Ti. One region of Ti, known as T-DNA (transferred DNA), contains genes which are not involved in the transfer process, making it possible to replace those genes with genes of interest for genetic engineering purposes. By a mechanism which remains unknown, although thought to be analogous to bacterial conjugation, the T-DNA is transferred into the plant cell and is stably inserted into the nuclear DNA in a process thought to involve proteins coded by the Vir E gene.

Expression and stable delivery of foreign genes into plants by *Agrobacterium*-mediated gene transfer has been demonstrated (Bevan et al., 1983; Fraley et al., 1983; Zambryski et al., 1983; Horsh et al., 1985). Since then, dicots have been identified as being the most efficient host for *Agrobacterium*-mediated transformation. Even though monocots are not the natural host of *Agrobacterium* (DeClene and Deley, 1976), there is now increasing evidence that, under certain conditions, *Agrobacterium* can be used to transform monocots (Bytebier et al., 1987; May et al., 1995; Ishida et al., 1996; Rashid et al., 1996).

Protoplast-Mediated Transformation

Protoplasts are plant cells whose cell wall has been removed by enzymes such as cellulase, pectolyase and macerozyme. These naked (plasma membrane) cells are surrounded by tiny pores, which are nevertheless too small for direct penetration of naked DNA (genes). However, the use of polyethylene glycol (PEG) or a short high-voltage electric pulse (electroporation) can produce transient pores, which allow DNA to enter the cells (Lorz et al., 1985). Transgenic monocot plants, produced using protoplasts have been reported (Horn et al., 1988; Rhodes et al., 1988; Shimamoto et al., 1989; Wang et al., 1992). The most significant disadvantage of using protoplast-mediated transformation is that the regeneration of whole plants from monocot protoplasts is very difficult (Potrykus, 1990).

Microprojectile Bombardment or Biolistics Transformation

Biolistics involves the use of an apparatus that accelerates DNA-coated high density metal particles at a high velocity sufficient to penetrate plant cell walls and membranes (Klein et al., 1987). The metal particles of about one to two microns in diameter are coated with a gene of interest prior to bombardment in the presence of Ca+ ions and spermidine. Small puncture holes produced on the cell walls and membranes after particle penetration will close spontaneously. This method has been the method of choice for monocots and most of the species which have failed to be transformed using *Agrobacterium*-mediated transfer or protoplast transformation have been successfully transformed using this method. The most commonly used tissue for biolistic-mediated transformation is derived from embryogenic suspension cultures (Fromm et al., 1990) and embryogenic callus cultures (Bower and Birch, 1992; Vasil et al., 1992). However, it was considered that transformation using primary explants with high regeneration capacity was superior (i.e. scutellar tissue can reduce the time required to produce transgenic plants and also reduce the risk of somaclonal variation (Christou et al., 1991; Jahne et al., 1995). Other tissues used for transformation and production of transgenic plants are protocorm (Kuehnle and Sugii, 1992) immature inflorescence (Barcelo et al., 1994), microspore (Jahne et al., 1994) and shoot meristem (Lowe et al., 1995) tissues. The only disadvantage of microprojectile bombardment is the low efficiency of obtaining stable transformation in comparison with transient expression.

Tissue Electroporation Transformation

Tissue electroporation has been used to transfer DNA into enzymatically or mechanically wounded tissue. Stably transformed maize type-1 callus and transgenic plants have been obtained using this method (D'Halluin et al., 1992). Other tissues that have been used for transformation are scutellum (Kloti et al., 1993), bisected mature embryos (Xu and Li, 1994), suspension culture cells (Laursen et al., 1994), embryogenic calli (Arencibia et al., 1995) and mechanically wounded immature embryo (Xiayi et al., 1996).

Silicon Carbide Transformation

This method involves mixing (e.g. by vortexing) cells in a solution containing whiskers (silicon carbide) and plasmid DNA. Collision between cells and whiskers results in cell penetration and delivery of DNA (Kaeppler et al., 1990). Fertile transgenic maize plants have been reported using suspension cultured cells (Frame et al., 1994).

Microinjection Transformation

Microinjection requires microcapillaries and microscopic equipment to deliver DNA directly into the nucleus. Injection results in a micro-hole on the cell wall, thought to have no effect on viability. This method has only been reported successfully in dicots (Schnorf et al., 1991; Bechtold et al., 1993). No success has yet been reported or confirmed in a monocot. The disadvantage of this method is that only one cell can be transferred per injection, making it a time consuming procedure.

Laser Microbeam Transformation

A laser microbeam can be used to overcome the cell wall barrier of cells, by punching a small hole on the surface via focusing the beam within the cell. This allows the manipulation of the nucleus or organelles without opening the cell membrane (Weber et al., 1990). The hole facilitates the entrance of foreign DNA into the cell and closes within 1-2 seconds (Weber et al., 1989). Production of transgenic plants has been reported (Guo et al., 1995). However, only GUS staining was used to prove that integration of the transgene into the regenerated plants had occurred. No Southern blot hybridization or progeny test data were shown in the report.

Imbibition of Seeds Transformation

The incubation of dry seeds or mature embryos in DNA solution has been shown to result in transformation (Topfer et al., 1989). This procedure is based on osmotic pressure differences forcing DNA into the seeds. However, no evidence of stable integration was provided.

DNA Integration

Transgene(s) needs to be stably integrated into the plant genome and subsequently expressed. The presence of the transgene can be confirmed by Southern blot hybridization (Sambrook et al., 1989) or polymerase chain reaction (PCR) (Chee et al., 1991). The presence of the transgene in the high molecular weigh undigested DNA as shown by Southern hybridization, is routinely used to confirm the total integration of the transgene (Casas et al., 1995). PCR is useful for screening a large quantity of samples but cannot be used to demonstrate the integration of the transgene.

Gene Expression (Protein)

Once transgene integration has been confirmed, it is important to determine whether the transgene is functional (expressed) in the transgenic plants. Method that can facilitate early detection of expression is the ability to detect survival in the presence of a selection agent, such as an antibiotic or a herbicide. The GUS reporter gene also can be used, together with a histochemical or fluorimetric assay, to examine gene expression early (Jefferson, 1987). Enzymatic assay for the detection of bar gene expression by acetylation of PPT in the presence of acetyl-CoA (DeBlock et al., 1987) can also facilitate early detection of transgene expression. Similar assays have been used for detection of hmr gene expression (Datta et al., 1990).

SUMMARY OF THE INVENTION

Throughout this specification unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

The present invention provides a method for producing transgenic plants and more particularly transgenic oil palm plants (*Elaeis* species). In accordance with the present invention, oil palm plants expressing a gene or genes which confer particular phenotypic traits, are provided. These genes may, for example, confer resistance to a herbicide, pest including a pathogenic agent or disease condition, or the genes may modify lipids and non-lipid components of palm oil resulting in improved quality of palm oil or altered or improved production of industrial oils and chemicals and/or the genes may encode nutraceutical and pharmaceutical compounds.

Accordingly, one aspect of the present invention contemplates a method for transforming cells of an oil palm plant with genetic material, said method comprising:

obtaining an explant from an oil palm plant;
establishing a transformable and regenerable embryonic callus therefrom;
transforming the said callus cells;
selecting for transformed calli.

Another aspect of the present invention provides a method for producing a genetically-modified and regenerated oil palm plant, said method comprising the further steps of:

maintaining said transformed calli for a time and under conditions sufficient for the formation of polyembryogenic callus cultures; and
regenerating transformed plantlets from said polyembryogenic callus cultures.

A preferred aspect of the present invention provides a method for the transformation and regeneration of an oil palm plant, said method comprising:

obtaining a root, leaf or inflorescence explant from an oil palm plant;
culturing said explant in callus-induction medium to generate embryogenic callus;
transforming said embryogenic callus;
selecting transformed embryogenic callus;
maintaining said transformed embryogenic callus for a time and under conditions sufficient for the formation of polyembryogenic callus cultures; and regenerating transformed plantlets from said polyembryogenic callus cultures.

Yet another preferred aspect of the present invention provides a method for the transformation and regeneration of an oil palm plant, said method comprising:
- obtaining an immature embryo explant from an oil palm plant;
- culturing said explant in 2,4-D-containing induction medium supplemented with thiamine or coconut water to generate embryogenic callus;
- transforming said embryogenic callus;
- selecting transformed embryogenic callus;
- maintaining said transformed embryogenic callus for a time and under conditions sufficient for the formation of polyembryogenic callus cultures; and
- regenerating transformed plantlets from said polyembryogenic callus cultures.

In still yet another aspect of the present invention, there is provided a method for the transformation and regeneration of an oil palm plant, said method comprising:
- obtaining an immature embryo explant from an oil palm plant;
- transforming said immature embryo explant;
- culturing said transformed immature embryo explant in callus-induction medium for a time sufficient to generate transformed Type II embryogenic callus;
- selecting transformed Type II embryogenic callus;
- maintaining said transformed Type II embryogenic callus for a time and under conditions sufficient for the formation of polyembryogenic callus cultures; and
- regenerating transformed plantlets from said polyembryogenic callus cultures.

A further aspect of the present invention provides a cell, tissue, or organ and particularly a cell, tissue, or organ from an oil palm plant, transfected or transformed according to the method of the present invention.

Yet another further aspect of the present invention provides a genetically modified oil palm plant cell or genetically-modified and regenerated multicellular oil palm plant or progeny thereof or parts of said transgenic oil palm plant, and includes genetically modified palm oil, produced by the genetically modified oil palm plant cell, or genetically-modified and regenerated multicellular oil palm plant or progeny thereof, or parts of said transgenic oil palm plant, generated in accordance with the methods of the present invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 8A, 8B and 8C are photographic representations showing Basta (registered trademark) treatment, via leaf painting, on leaves of transformed and untransformed oil palm, two weeks after treatment. 8A: Two leaves from one transgenic plant, painted with 0.03% v/v Basta (registered trademark) solutions containing 0.1% v/v Tween 20 and 0.1% v/v Triton X-100. 8B: Two leaves from one untransformed oil palm plant painted with 0.015% v/v (half strength) Basta (registered trademark) solutions containing 0.1% v/v Tween 20 and 0.1% v/v Triton X-100. 8C: Two leaves from one untransformed oil palm plant painted with 0.03% v/v Basta (registered trademark) solutions containing 0.1% v/v Tween 20 and 0.1% v/v Triton X-100.

Figure 1A:
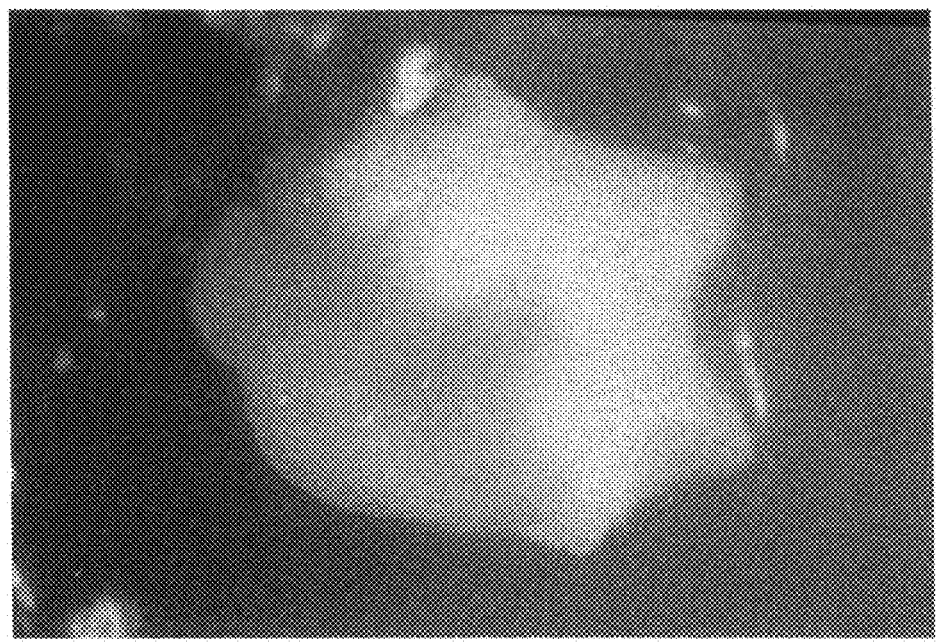
FIGS. 1A and 1B are photographic representations showing transient gusA gene expression (GUS activity) in oil palm embryogenic calli after DNA deliver. 1A: control (without DNA), and 1B: bombarded with pAHC27.

| ABBREVIATIONS | |
|---|---|
| ABBREVIATION | MEANING |
| GUS/gus | β-glucuronidase |
| MS | Murashige and Skoog salts |
| PAT | phosphinothricin acetyl transferase |
| PCR | polymerase chain reaction |
| ppm | part per million |
| PPT | phosphinothricin |
| TREC | transformable and regenerable embryogenic calli |
| Ubi1 | ubiquitin 1 |

DETAILED DESCRIPTION OF THE PREFERRED EMBODIMENTS

The present invention is directed to a method for the transformation of monocotyledonous cells of oil palm and to methods of regenerating transgenic plantlets therefrom.

The ability to produce transgenic oil palm plants facilitates the further improvement of this crop by the introduction of useful traits to generate, for example, plants which exhibit increased yield of oil, resistance to attack by diseases including those caused by pathogenic agents, modified lipids and non-lipid components of palm oil and improve the quality of palm oil or improved production of industrial oils and chemicals or the traits may include the production of nutraceutical and pharmaceutical compounds.

Accordingly, one aspect of the present invention contemplates a method for transforming cells of an oil palm plant with genetic material, said method comprising:

obtaining an explant from an oil palm plant;
establishing a transformable and regenerable embryogenic callus therefrom;
transforming the said callus cells;
selecting for transformed calli.

In a related embodiment, the present invention provides a method for producing a genetically-modified and regenerated oil palm plant, said method comprising the further steps of:

maintaining said transformed calli for a time and under conditions sufficient for the formation of polyembryogenic callus cultures; and
regenerating transformed plantlets from said polyembryogenic callus cultures.

The term "genetically modified" is used in its broadest sense to include introducing exogenous genetic material such as in the generation of a transgenic plant as well as inducing a mutation in the genome of a plant cell. The term also encompasses introducing antisense molecules, ribozymes and sense molecules such as for use in co-suppression. A "mutation" includes the introduction of a single or multiple nucleotide substitution, addition and/or deletion. The genetic material to be introduced may be a gene or may correspond to a gene or may be a gene fragment, segment, portion and/or a gene hybrid or fusion or a combination of genes. The genes may be in monocistronic form or in multicistronic form.

The term "gene" is used in its broadest sense and includes cDNA corresponding to the exons of a gene. Accordingly, reference herein to a "gene" is to be taken to include:
(i) a classical genomic gene consisting of transcriptional and/or translational regulatory sequences and/or a coding region and/or non-translated sequences (i.e. introns, 5'- and 3'-untranslated sequences); or
(ii) mRNA or cDNA corresponding to the coding regions (i.e. exons) and 5'- and 3'-untranslated sequences of the gene.

The term "gene" is also used to describe synthetic or fusion molecules encoding all or part of a functional product.

The genetic material may be in the form of a genetic construct comprising a gene or nucleic acid molecule to be introduced into a plant cell, operably linked to a promoter and optionally various regulatory sequences.

The genetic material of the present invention may comprise a sequence of nucleotides or be complementary to a sequence of nucleotides which comprise one or more of the following: a promoter sequence, a 5' non-coding region, a cis-regulatory region such as a functional binding site for transcriptional regulatory protein or translational regulatory protein, an upstream activator sequence, an enhancer element, a silencer element, a TATA box motif, a CCAAT box motif, or an upstream open reading frame, transcriptional start site, translational start site, and/or nucleotide sequence which encodes a leader sequence.

The term "5' non-coding region" is used herein in its broadest context to include all nucleotide sequences which are derived from the upstream region of an expressible gene, other than those sequences which encode amino acid residues which comprise the polypeptide product of said gene, wherein the 5' non-coding region confers or activates or otherwise facilitates, at least in part, expression of the gene.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. The present invention extends to any promoter or promoter element recognized by one or more of a type I, II and/or III DNA polymerase.

In the present context, the term "promoter" is also used to describe a synthetic or fusion molecule, or derivative which confers, activates or enhances expression of a structural gene or other nucleic acid molecule, in a plant cell. Preferred promoters according to the invention may contain additional copies of one or more specific regulatory elements to further enhance expression in a cell, and/or to alter the timing of expression of a structural gene to which it is operably connected.

Promoter sequences contemplated by the present invention may be native to the host plant to be transformed or may be derived from an alternative source, where the region is functional in the host plant. Other sources include the *Agrobacterium* T-DNA genes, such as the promoters for the biosynthesis of nopaline, octapine, mannopine or other opine promoters; promoters from plants, such as the ubiquitin promoter; tissue specific promoters (see e.g. U.S. Pat. No. 5,459,252 to Cockling et al.; WO 91/13992 to Advanced Technologies); promoters from viruses (including host specific viruses) or partially or wholly synthetic promoters. Numerous promoters that are functional in mono- and dicotyledonous plants are well known in the art (see, for example, Greve, 1983; Salomon et al., 1984; Garfinkel et al., 1983; Barker et al, 1983); including various promoters isolated from plants (such as the Ubi promoter from the maize ubi-1 gene, Christensen and Quail, 1996) (see, e.g. U.S. Pat. No. 4,962,028) and viruses (such as the cauliflower mosaic virus promoter, CaMV 35S).

The term "operably connected" or "operably linked" in the present context means placing a structural gene under the regulatory control of a promoter which then controls expression of the gene. Promoters and the like are generally positioned 5' (upstream) to the genes which they control. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e. the genes from which it is derived.

The transformation and regeneration method of the present invention employs explant material as a source for establishing embryogenic and polyembryogenic callus. The embryogenic calli may be derived from either solid or liquid medium.

Any suitable source of explant material may be used including, for example, shoot, root, leaf, inflorescences, petiole, immature embryo. Particularly preferred explant materials are root, leaf and both male and female inflorescences. Following culturing in appropriate callus-induction medium, these materials form transformable embryogenic calli cells, which may be maintained in agar-solidified nutrient media or in liquid medium, well known to those skilled in the art of tissue culture. A further suitable source of explant material is immature embryos, which also form transformable embryogenic callus following culturing in 2,4-D-containing induction medium, if supplemented with either thiamine or coconut water.

Embryogenic calli cells are then transformed with the desired genetic material, following which transformed polyembryogenic cell cultures are generated which are then used to regenerate genetically-transformed plantlets.

Accordingly in one preferred embodiment, the present invention provides a method for the transformation and regeneration of an oil palm plant, said method comprising:
  obtaining a root, leaf or inflorescences explant from an oil palm plant;
  culturing said explant in callus-induction medium to generate embryogenic callus in solid or liquid medium;
  transforming said embryogenic callus;
  selecting transformed embryogenic callus;
  maintaining said transformed embryogenic callus for a time and under conditions sufficient for the formation of polyembryogenic callus cultures; and
  regenerating transformed plantlets from said polyembryogenic callus cultures.

In a related embodiment, the present invention provides a method for the transformation and regeneration of an oil palm plant, said method comprising:
  obtaining an immature embryo explant from an oil palm plant;
  culturing said explant in 2,4-D-containing induction medium supplemented with thiamine or coconut water to generate embryogenic callus;
  transforming said embryogenic callus;
  selecting transformed embryogenic callus;
  maintaining said transformed embryogenic callus for a time and under conditions sufficient for the formation of polyembryogenic callus cultures; and
  regenerating transformed plantlets from said polyembryogenic callus cultures.

Concentrations of media supplements should be in the range 0.1-2.0 g/l, preferably 0.25-1.0 g/l and even more preferably 0.4-0.6 g/l thiamine, and 50-200 ml/l, preferably 75-150 ml/l and even more preferably 90-120 ml/l coconut water. Those skilled in the art will appreciate that the concentration may be varied somewhat and still be effective for the desired purpose. Preferably, the 2,4-D-containing callus induction medium is supplemented with coconut water.

In a particularly preferred embodiment, a root or leaf or inflorescences or immature embryo explant is cultured in appropriate callus-induction medium for a time sufficient to generate Type II embryogenic callus, which is subjected to selection, and transformed Type II embryogenic callus is subsequently maintained for a time and under conditions sufficient for the formation of polyembryogenic callus cultures which are able to be regenerated transformed into transformed plantlets.

As will be appreciated by a person skilled in the relevant art, in seeking suitable explant material for transformation and subsequent selecting and regeneration, and/or for generation of transformable callus and subsequent selecting and regeneration, it is not always critical that the steps of callus formation and transformation be carried out in a particular specified order. Reversal of the order of some steps and features may be possible without adversely affecting the desired outcome. Hence, in a further embodiment, embryos are first transformed with the desired genetic material, following which embryogenic calli cells are induced, the desired Type of transformed embryogenic calli selected, and used to generate polyembryogenic cell cultures that are able to be regenerated to form genetically-transformed plantlets.

Accordingly, in another preferred embodiment of the present invention, there is provided a method for the transformation and regeneration of an oil palm plant, said method comprising:
  obtaining an immature embryo explant from an oil palm plant;
  transforming said immature embryo explant;
  culturing said transformed immature embryo explant in callus-induction medium for a time sufficient to generate transformed Type II embryogenic callus;
  selecting transformed Type II embryogenic callus;
  maintaining said transformed Type II embryogenic callus for a time and under conditions sufficient for the formation of polyembryogenic callus cultures; and
  regenerating transformed plantlets from said polyembryogenic callus cultures.

Suitable methods for introduction of genetic material into cells include transformation using $CaCl_2$ and variations thereof, direct DNA uptake into protoplasts, PEG-mediated uptake to protoplasts, microparticle bombardment, electroporation, microinjection, microparticle bombardment of tissue explants or cells, vacuum-infiltration of tissue with nucleic acid and T-DNA-mediated transfer from *Agrobacterium* to the plant tissue.

*Agrobacterium*-mediated transformation may be effected by co-cultivating an explant to be transfected with *Agrobacterium* species having a T-DNA or T-DNA region comprising the genetic material to be transformed into the plant cells, for a time and under conditions sufficient for the genetic material to transfer into the plant cells. The *Agrobacterium* species may be either high or low virulent strain. A particularly useful *Agrobacterium* species is *Agrobacterium tumefaciens* strain AGL0 (Lazo et al., 1991), AGL1 (Lazo et al., 1991), strain ICMP 8317 (Janssen and Gardner, 1989), strain EHA101 (Hood et al., 1986), strain LBA4404 (Hoekema et al., 1983) and strain C58 (Konez and Schell, 1986).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 0.1 to 10 μm and more particularly 10.5 to 5 μm tungsten or gold spheres. The genetic construct may be deposited on the microparticle by any suitable technique, such as by precipitation.

In a particularly preferred embodiment of the present invention, the introduction of desired genetic material into the cells of embryogenic callus including suspension embryogenic callus or immature embryo explant of an oil palm plant is effected via a microparticle bombardment.

The genetic transformation and regeneration methods of the present invention may be employed to confer on a plant cell and, in particular, an oil palm plant cell, specifically-desired traits such as, for example, an increased yield of oil, resistance to disease conditions including attack by disease-causing pathogenic agents, a trait may result in a modified lipid or non-lipid component of palm oil and/or a trait may improve the quality of palm oil, production of industrial oils and chemicals and nutraceutical and pharmaceutical compounds, to name but a few. Useful genes and their modified versions for effecting such outcomes includes but is not limited to, inter alia, acetyl CoA carboxylase (ACCase), chitinase, glucanase, cry (*Bacillus thuringiensis*), β-ketoacyl ACP synthase II (KASII), ketoacyl ACP synthase I (KASI), ketoacyl ACP synthase III (KASIII), palmitoyl ACP thioesterase and other thioesterases, stearoyl ACP desaturase and other desaturases, oleoyl CoA desaturase, fatty acid elongases, oleate hydroxylase, acyltransferases, β-ketothiolase, threonine deaminase/dehydratase, acetoacetyl CoA reductase and polyhydroxybutyrate synthase. Besides the above genes, targeting the products into specific tissues is also important. For oil palm, mesocarp is the tissue where oil is synthesized, so targeting the gene expression into the mesocarp is important. Therefore, isolation of tissue-specific promoter is essential. Useful promoters for effecting such outcomes include, inter alia, mesocarp specific, kernel specific, leaf specific and root specific.

In accordance with the present invention, a genetic construct comprising a desired trait may be incorporated into a plasmid capable of replicating in an oil palm cell, coated onto gold or tungsten microparticles by, for example, precipitation and bombarded into embryogenic callus to produce transformed callus cells, capable of being regenerated into transgenic oil palm plantlets. The transformed embryogenic callus cells of the present invention are selected under any one of a number of suitable selective agents well known to those skilled in the art. Alternatively, the said gold or tungsten microparticles may be bombarded into immature embryos from which selected transformed embryogenic callus, capable of being regenerated into transgenic oil palm plantlets, is induced to form.

To facilitate identification of transformed cells, the embryogenic callus is bombarded with a further genetic construct, comprising a selectable or screenable marker gene. The actual choice of a marker is not crucial as long as it is functional (i.e. selective) in combination with the plant cells of choice. The marker gene and the gene of interest do not have to be linked, since co-transformation of unlinked genes as, for example, described in U.S. Pat. No. 4,399,216 is also an efficient process in plant transformation.

Included within the terms "selectable or screenable marker genes" are genes that encode a "secretable marker" whose secretion can be detected as a means of identifying or selecting for transformed cells. Examples include markers that encode a secretable antigen that can be identified by antibody interaction or secretable enzymes that can be detected by their catalytic activity. Secretable proteins include, but are not restricted to, proteins that are inserted or trapped in the cell wall (e.g. proteins that include a leader sequence such as that found in the expression unit of extension or tobacco PR-S); small, diffusible proteins detectable, for example, by ELISA; and small active enzymes detectable in extracellular solution such as, for example, β-amylase, β-lactamase, phosphinothricin acetyltransferase).

Examples of bacterial selectable markers are the dal genes from *Bacillus subtilis* or *Bacillus licheniformis*, or markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (neo) gene conferring resistance to kanamycin, paromomycin, G418 and the like as, for example, described by Potrykus et al., (1985); a glutathione-S-transferase gene from rat liver conferring resistance to glutathione derived herbicides as, for example, described in EP-A 256 223; a glutamine synthetase gene conferring, upon overexpression, resistance to glutamine synthetase inhibitors such as phosphinothricin as, for example, described WO87/05327, an acetyl transferase gene from *Streptomyces viridochromogenes* conferring resistance to the selective agent phosphinothricin as, for example, described in EP-A 275 957, a gene encoding a 5-enolshikimate-3-phosphate synthase (EPSPS) conferring tolerance to N-phosphonomethylglycine as, for example, described by Hinchee et al., 1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP-A-154 204); or a mutated anthranilate synthase gene that confers resistance to 5-methyl tryptophan.

Preferred screenable markers include, but are not limited to, a uidA gene encoding a β-glucuronidase (GUS) enzyme for which various chromogenic substrates are known; a β-galactosidase gene encoding an enzyme for which chromogenic substrates are known; an aequorin gene (Prasher et al., 1985), which may be employed in calcium-sensitive bioluminescence detection; a green fluorescent protein gene (Niedz et al., 1995); a luciferase (luc) gene (Ow et al., 1986), which allows for bioluminescence detection; β-lactamase gene (Sutcliffe, 1978), which encodes an enzyme for which various chromogenic substrates are known (e.g. PADAC, a chromogenic cephalosporin); an β-locus gene, encoding a product that regulates the production of anthocyanin pigments (red colour) in plant tissues (Dellaporta et al., 1988); an α-amylase gene (Ikuta et al., 1990); a tyrosinase gene (Katz et al., 1983) which encodes an enzyme capable of oxidizing tyrosine to dopa and dopaquinone which in turn condenses to form the easily detectable compound melanin; or a xylE gene (Zukowsky et al., 1983), which encodes a catechol dioxygenase that can convert chromogenic catechols.

As will also be appreciated by a person skilled in the relevant art, media components suitable for effecting the formation of transformed polyembryogenic callus from transformed embryogenic callus are many and varied. Such components may include but are not limited to sugars, amino acid and vitamin supplements, and growth promoting hormones such as auxins and cytokines. Sometimes, an improvement in the speed or efficacy of the desired outcome may be achieved by manipulation of these components and the concentrations at which they are present. In accordance with the present invention, preferred components have been found to include an auxin, such as napthalene acetic acid, indole acetic acid or indole butyric acid.

Preferably the auxin is indole butyric acid. In a particularly preferred embodiment, indole butyric acid is present in the medium at a concentration in the range 1-10 µM, preferably 3-8 µM and even more preferably 4-6 µM. Those skilled in the art will appreciate that the concentration may be varied somewhat and still be effective for the desired purpose.

The method of the present invention is initiated by obtaining an explant from a plant, generally in the form of leaf, root or inflorescences tissue or an immature embryo. After sterilization, the explant is transferred to callus induction medium, comprising for example, MS salts and $Y_3$ vitamins supplemented appropriately, and incubated at 28° C. in the dark. For leaf and root explants, supplements include myo-Inositol, L-glutamine, sucrose, activated charcoal, agar and an auxin, such as for example, 4-dichlorophenoxyacetic acid (2,4-D). For immature embryo explants, supplements include myo-Inositol, L-glutamine, sucrose, NaFeEDTA and, preferably, thiamine or coconut water. Coconut water, at a concentration of 50-150 ml/l and more preferably 100 ml/l, is a particularly-preferred supplement.

For leaf and root explants, incubation continues for a period of about 6-8 weeks or until the beginning of production of embryogenic calli, following which the cultures are sub-cultured every 12 weeks. In the case of immature embryo explants, incubation continues with sub-culturing every 3-4 weeks, for up to 12 weeks or until embryogenic calli were produced.

Embryogenic calli are maintained on embryogenic medium, comprising, for example, MS salts, macro- and micro-nutrients and $Y_3$ vitamins supplemented with myo-Inositol, L-glutamine, L-asparagine, sucrose and auxins, such as for example, 10 μM 2,4-D and 5 μM napthalene acetic acid (NAA), and are incubated at 28° C. in the dark. Embryogenic calli are sub-cultured every 30 days into fresh nutrient medium. During maintenance of said embryogenic callus cultures, distinct morphological Types (I, II and III) of embryogenic callus are obtained.

Type I, Type II or Type III embryogenic callus, and preferably Type II embryogenic callus, is subjected to transformation via microparticle bombardment of gold particles, having diameter of preferably 0.1-3.0 microns, more preferably 0.5-2.0 microns and still more preferably 0.8-1.2 microns, onto which has been precipitated a desired-DNA-containing genetic construct. Gold particles are bombarded into preferably 0.1-2.0 grams wet weight of embryogenic callus, more preferably 0.3-1.0 gram wet weight of embryogenic callus, and still more preferably 0.5-0.7 gram wet weight of embryogenic callus.

The putatively-transformed embryogenic callus cultures are then subjected to selection under an appropriate selection environment. For example, selection of transformed cells may be achieved using a variety of chemical agents, such as antibiotics (e.g. hygromycin and/or geneticin (G418)) or herbicides (e.g. Basta (trademark)). Use of these agents may require the inclusion of a selectable marker gene, such as but not limited to the hph gene for hygromycin resistance or the nptII gene for geneticin or kanamycin resistance, and the bar gene for Basta (trademark) resistance. These genes render the transformed cells resistant to the selection agent.

One particularly useful selection medium comprises Basta (13.5% PPT) at concentrations of about 35-45 ppm, and preferably 40 ppm, to about 75-85 ppm and preferably 80 ppm, or at gradually increasing concentrations of from about 5-15 ppm, and preferably 10 ppm, to about 15-25 ppm, and preferably 20 ppm, and finally to about 35-45 ppm, and preferably 40 ppm at 3 weeks post-bombardment.

Following selection, transformed embryogenic callus cultures are generally transferred to polyembryogenic-inducing medium, comprising for example, MS salts, macro- and micro-nutrients and $Y_3$ vitamins supplemented with myo-Inositol, L-glutamine, L-asparagine, L-arginine, sucrose and agar, and an auxin, such as for example, 5 μM indole butyric acid (IBA), in which they are cultured for generally at least about 3-6 months, more usually at least about 3-4 months and preferably at least 4 months, with sub-culturing into fresh medium generally every 20-40 days, more particularly every 25-35 days and preferably about every 30 days, until the formation of green-coloured polyembryogenic cultures.

Transformed polyembryogenic cultures are finally transferred to an appropriate shoot-inducing medium, such as, for example, MS salts, macro- and micro-nutrients and $Y_3$ vitamins, supplemented with myo-inositol, L-glutamine, L-asparagine, L-arginine, sucrose and agar, and an auxin such as for example 0.1 μM NAA. Normally, shoot induction requires at least about 2-4 months, and more usually at least about 3 months. Propagation of shoots generally requires an auxin, such as NAA. Production of roots generally requires a further auxin, such as for example 2,4-D, in addition to NAA. Other possibly suitable auxins include indole acetic acid (IAA) and IBA. Accordingly, roots are induced in medium supplemented as above, but with the addition of 10 μM 2,4-D, 70 μM NAA, and activated charcoal. After incubation at 28° C. for at least about 2 months, the plantlets are then transferred to soil.

Accordingly, a further aspect of the present invention provides a cell, tissue, or organ and particularly a cell, tissue, or organ from an oil palm plant, transfected or transformed according to the method of the present invention. This aspect of the present invention further extends to progeny of the said oil palm plants, transformed according to the method of the instant invention, as well as to vegetative, propagative and reproductive parts of said plants, and to reproductive portions including cuttings, pollen, seeds, embryos, callus and embryogenic callus.

Yet another aspect of the present invention provides a genetically modified oil palm plant cell or genetically-modified and regenerated multicellular oil palm plant or progeny thereof or parts of said transgenic oil palm plant.

More particularly, in this aspect of the present invention, there is provided genetically modified palm oil, produced by the genetically modified oil palm plant cell, or genetically-modified and regenerated multicellular oil palm plant or progeny thereof, or parts of said transgenic oil palm plant, produced in accordance with the methods of the present invention The present invention is further described by the following non-limiting Examples.

Example 1

Plant Material

Leaf, root and inflorescences explants were derived from the clone MS3399-P13 MPOB, Serdang. Leaf, roots and inflorescences explants were derived from both matured and in vitro plantlets. Immature embryos were derived from 0.230/84 and 0.230/86 MPOB, UKM.

Example 2

Embryogenic Callus Initiation and Proliferation

Callus was successfully produced from all the explants cultured.

(i) Embryogenic Calli Initiation from Leaflet and Roots

Leaflets of unopened (−6) frond, root (after disinfecting using 5% of sodium hypochlorite for 5 minutes and at least 5 times with sterilized dionized water), inflorescences and in vitro plantlets from various clones were aseptically transferred to solid, autoclaved (15 psi, 121° C., 20 minutes) callus initiation medium [MS salts (Murashige and Skoog, 1962)+ Y3 vitamins (Eeuwans, 1976)+0.1 g/l myo-Inositol and L-glutamine+3% sucrose+5×10$^{-5}$M 2,4-dichlorophenoxyacetic acid (2,4-D)+0.25% activated charcoal+0.7% agar (Sigma, A7002)] and incubated at 28° C. in the dark (Paranjothy et al., 1989).

Callus started to be produced from leaf, root and inflorescences explants at least 6-8 weeks after culture on callus induction medium. Explants with the callus were subcultured every 12 weeks on the same medium until embryogenic calli were formed. The embryogenic callus normally needed at least 24 to 36 weeks to be produced from ordinary callus.

(ii) Embryogenic Callus Initiation from Immature Embryos

Immature embryos were collected 13-15 weeks after anthesis. After sterilization (using 5% sodium hypochlorite for 5 minutes and at least 5 times with sterilized deionized water), callus was initiated using 14 different combinations of immature embryo callus induction medium (IEC). The common basic ingredients were: MS macro salt+Y3 micro+Y3 vitamins+0.0375 g/l NaFeEDTA, +0.1 g/l myo-Inositol and 0.1 g/l L-glutamine. The rest were as follow:

IEC1: 10$^{-5}$M 2,4-D, 30 g/l sucrose and 2.5 g/l gelrite;

IEC2: 10$^{-5}$M 2,4-D, 30 g/l sucrose and 5.0 g/l gelrite;

IEC3: 10$^{-4}$M 2,4-D, 30 g/l sucrose, 6 g/l agar and 3 g/l activated charcoal;

IEC4: 10$^{-4}$M 2,4-D, 30 g/l sucrose, 10 g/l agar and 3 g/l activated charcoal;

IEC5: 10$^{-5}$M 2,4-D, 60 g/l sucrose and 2.5 g/l gelrite;

IEC6: 2.5×10$^{-5}$M 2,4-D, 30 g/l sucrose and 2.5 g/l gelrite;

IEC7: 5×10$^{-5}$M 2,4-D, 30 g/l sucrose and 2.5 g/l gelrite;

IEC8: 10$^{-5}$M 2,4-D, 30 g/l sucrose, 0.3 g/l casein hydrolysate and 2.5 g/l gelrite;

IEC9: 10$^{-5}$M 2,4-D, 30 g/l sucrose, 0.5 g/l proline and 2.5 g/l gelrite;

IEC10: 10$^{-5}$M 2,4-D, 30 g/l sucrose, 0.5 g/l thiamine and 2.5 g/l gelrite;

IEC11: 10$^{-5}$M 2,4-D, 30 g/l sucrose, 10$^{-6}$ M 2,4,5-Trichlorophenoxyacetic acid [2,4,5-T] and 2.5 g/l gelrite;

IEC12: 10$^{-5}$M 2,4-D, 30 g/l sucrose, 100 ml/l coconut water and 2.5 g/l gelrite;

IEC13: 10$^{-4}$M NAA, 30 g/l sucrose and 2.5 g/l gelrite; and

IEC14: 2×10$^{-4}$M NAA, 30 g/l sucrose and 2.5 g/l gelrite.

Explants were incubated at 28° C. in the dark. Explants and calli were subcultured into fresh immature embryo-callus-induction medium every 12 weeks until embryogenic calli were produced.

Callus started forming from the immature embryo explants at least 3 weeks after subculture in all the 14 combinations of immature embryo callus induction medium tested. However, the efficiency of producing embryogenic calli, polyembryogenic calli, shoots and roots varies from medium to medium. Table 1 summarizes the effect of all 14 media. It was found that only in IEC10 and IEC12 media were immature embryo explants able to be regenerated into plants. The basic requirements for regeneration from immature embryos were 2,4-D and gelrite with, importantly, the addition of coconuts water or thiamine. No regeneration was obtained in medium containing NAA and agar. Coconut water was preferred, due to its ability to produce the highest number of plantlets.

(iii) Maintenance of the Embryogenic Calli

The embryogenic calli from all explant types were maintained on agar (Sigma A7002)-solidified embryogenic medium containing MS macro- and micronutrients and Y$_3$ vitamins supplemented with 100 mg/l each of myo-inositol, L-glutamine and L-asparagine, 10 µM 2,4-D, 5 µM α-Naphthaleneacetic acid (NAA) and 30 g/l sucrose. The medium was adjusted to pH 5.7 with KOH prior to autoclaving (15 psi, 121° C., 20 minutes) (Paranjothy et al., 1989). Embryogenic calli were incubated at 28° C. in the dark and were subcultured every 30 days into fresh medium.

The embryogenic calli were maintained on embryogenic medium until they reached the right stage for bombardment and proliferation.

TABLE 1

| Medium | % Callus | % Embryogenic calli | % Polyembryogenic | No. Plantlets |
|---|---|---|---|---|
| IEC1 | 100 | 5 | 1 | 0 |
| IEC2 | 100 | 0 | | |
| IEC3 | 100 | 0 | | |
| IEC4 | 100 | 0 | | |
| IEC5 | 100 | 5 | 0 | |
| IEC6 | 100 | 0 | | |
| IEC7 | 100 | 0 | | |
| IEC8 | 100 | 0 | | |
| IEC9 | 100 | 10 | | |
| IEC10 | 100 | 25 | 15 | 92 |
| IEC11 | 100 | 10 | 0 | |
| IEC12 | 100 | 25 | 15 | 173 |
| IEC13 | 90 | 5 | 0 | |
| IEC14 | 65 | 0 | | |

Percentages of callus, embryogenic and polyembrogenic are the mean of 2 clones and 20 immature embryos per medium per clone. No. of plantlets is the total number of plantlets obtained from the initial 20 embryos cultured.

(iv) Proliferation of Embryogenic Calli

Three morphological types of embryogenic callus were obtained using the embryogenic media: Type I, Type II and Type III. All three were isolated, bombarded and subjected to selection, proliferation and regeneration. One of the embryogenic callus types (Type II, designated TREC), was successfully used to produce transgenic plants. See Example 3, below.

(iv) Initiation of Suspension Embryogenic Calli Cultures

Friable and grainy embryogenic calli from solid medium were transferred into liquid medium containing MS macro- and micronutrients and Y$_3$ vitamins supplemented with 100 mg/l each of myo-inositol, L-glutamine and L-asparagine, 25 µM 2,4-D and 30 g/l sucrose. The medium was adjusted to pH 5.7 with HCl/NaOH prior to autoclaving (15 psi, 121° C., 20 minutes) (Tarmizi et al., 1999). Embryogenic suspension calli were incubated in 12 hrs/12 hrs light/dark photoperiod at 28° C.-30° C. and placed on orbital shakers at 100 rpm. Based on the sieve used, the suspension were divided into two different types, >1.0 mm <3.0 mm and <1.0 mm aggregates.

(v) Maintenance of the Suspension Embryogenic Calli Cultures

The established embryogenic suspension calli were maintained in liquid medium containing MS macro- and micronutrients and Y$_3$ vitamins supplemented with 100 mg/l each of myo-inositol, L-glutamine and L-asparagine, 25 µM 2,4-D and 30 g/l sucrose. The medium was adjusted to pH 5.7 with HCl/NaOH prior to autoclaving (15 psi, 121° C., 20 minutes) (Tarmizi et al., 1999). Suspensions were incubated in 12 hrs/12 hrs light/dark photoperiod at 28° C.-30° C. an placed on orbital shakers at 100 rpm. Suspensions were subcultures by sieving them according to the size of the aggregates at monthly interval into fresh medium. Based on the sieve used, the suspension were divided into two aggregates sizes: >1.0 mm <3.0 mm and <1.0 mm aggregates. The cultures were maintained in the same media formulation for further proliferation and to different media for induction of maturation.

(vii) Initiation and Production of Polyembryogenic Cultures

Embryogenic cultures from solid and liquid suspension medium were transferred onto polyembryogenic-inducing medium containing MS macro- and micronutrients and $Y_3$ vitamins supplemented with 100 mg/l each of myo-inositol, L-glutamine, L-arginine and L-asparagine, 5 µM Indole-3-butyric acid (IBA), 0.7% agar and 30 g/l sucrose to form polyembryogenic cultures. The medium was adjusted to pH 5.7 with KOH prior to autoclaving (15 psi, 121° C., 20 minutes) (Paranjothy et al., 1989). Embryogenic calli were incubated at 28° C. in the presence of light and were subcultured every 30 days into fresh medium.

Green-coloured polyembryogenic cultures were obtained after at least 4 months on the polyembryogenic inducing medium. Once the polyembryogenic calli were big enough for regeneration, they were transferred into different media for shoot induction. It was observed that only Types II and III embryogenic calli were able to produce polyembryogenic cultures once exposed to light. The Type I failed to produce polyembryogenic calli, even after 9 month on polyembryogenic inducing medium. Type I calli was, thus, not competent for regeneration.

Example 3

Plant Regeneration (i) Small Plantlet Production from Polyembryogenic Cultures

Small plantlets were produced from polyembryogenic cultures on shoot-inducing medium containing MS macro- and micronutrients and $Y_3$ vitamins supplemented with 100 mg/l each of myo-inositol, L-glutamine, L-arginine and L-asparagine, 0.1 µM NAA, 0.4% agar and 30 g/l sucrose. The medium was adjusted to pH 5.7 with KOH prior to autoclaving (15 psi, 121° C., 20 minutes) (Paranjothy et al., 1989). Polyembryogenic calli were incubated at 28° C. in light for sufficient time to permit the initiation of shoots from the calli cells.

It was found that shoots were induced more efficiently in conical flasks, compared to Petri dishes. Normally at least 3 months were needed for the first shoots to be produced from the polyembryogenic cultures, on the shoot-inducing medium. The polyembryogenic cultures were subcultured continuously until large enough shoot clumps had been produced. The shoot clumps were then isolated and transferred into a different medium to produce roots.

(ii) Root Initiation

Roots were initiated from small plantlets in test tubes filled with 10 ml of liquid root-inducing medium containing MS macro- and micronutrients and $Y_3$ vitamins supplemented with 300 mg/l L-glutamine, 100 mg/l myo-inositol, 10 µM 2,4-D, 70 µM NAA, 0.15% activated charcoal and 60 g/l sucrose. The medium was adjusted to pH 5.7 with KOH prior to autoclaving (15 psi, 121° C., 20 minutes) (Paranjothy et al., 1989). Plantlets were incubated at 28° C. in light until roots had formed.

At least two months were usually needed for roots to be produced from individually isolated shoot clumps. Once the roots were big enough, the plantlets were transferred into polybags containing soil and kept in the nursery for further growth.

Example 4

DNA Delivery, Selection of Transformants and Regeneration of Transgenic Plants (i) Large Scale Plasmid Isolation One milliliter of overnight bacterial cultures containing pAHC20 and pAHC27 plasmids were inoculated to 500 ml of LB media (5 g NaCl, 5 g tryptone and 2.5 g yeast extract) containing 75 µg/ml of antibiotic (ampicillin). The overnight cultures was transferred to large centrifuge bottles and bacteria were pelleted by centrifuging (4,000 rpm, 10 min and 4° C.). Isolation was carried out according to Sambrook et al., 1989.

The pellet was resuspended in 5 ml of ice cold solution I (25 mM Tris-HCl, 10 mM $Na_2$-EDTA, 50 mM glucose pH 8.0 (5 mg/ml lysozyme)) and the mixture was kept at room temperature (RT) for 5 min. Ten milliliters solution II (0.2 M NaOH, 1% w/v SDS) was added, mixed by gentle inverting and incubated on ice for 10 min. Seven and a half ml of solution III (5M KAc) was added, mixed vigorously and incubated on ice for 10 min. Lysate was spun down (12,000 rpm, 15 min and 4° C.) and the supernatant was filtered through one layer of miracloth into a new centrifuge tube. To each tube, 0.6 volumes of isopropanol was added, mixed gently and left at RT for 15 min. Nucleic acids were pelleted (12,000 rpm, 15 min and RT), rinsed with 70% ethanol and dried at RT for 30 min.

The pellet was resuspended by adding 4 ml of TE buffer (10 mM Tris, 1 mM EDTA, pH 8.0), gently vortexed and treated with RNase (75 µl (5 mg/ml), 15 min and 37° C.). DNA solution was transferred to a preweighed graded 15 ml centrifuge tube, 1 g/ml of CsCl was added and dissolved by inverting the tube. Ethidium bromide (EtBr) was added (0.4 ml (10 mg/ml)), mixed and centrifuged in a table top centrifuge (max speed, 5 min and RT). The clear red solution was transferred to a Beckman quick-seal tube with a needle attached to a syringe and filled to the neck of the tube. The tube was balanced, sealed and centrifuged (60,000 rpm, 20 hr and 20° C.). The lower band (circular plasmid DNA) was removed with a needle attached to a syringe and collected in a 5 ml plastic tube. EtBr was removed by 4-5 times isoamyl alcohol extractions. CsCl was removed by diluting the content with 3×$H_2O$ and precipitated by adding 8× ethanol. The pellet was dissolved in TE (pH 8.0) buffer, the concentration assessed by measurement of O.D. at $A_{260}/A_{280}$, and an aliquot digested with appropriate restriction enzymes and run on agarose gel.

(ii) DNA Delivery in Embryogenic Calli

DNA precipitation onto gold or tungsten microcarriers was carried out according to the instruction manual for the Biolistic PDS/He 1000 device (BioRad Laboratories, Hercules, Calif., USA). Gold microcarriers (1.0 micrometer; BioRad) were used at a concentration of 60 mg/ml in absolute ethanol.

Suspensions were vortexed vigorously for 1-2 minutes to remove aggregated lumps. This was repeated three times. The suspensions were spun for 1 minute at 10,000 rpm and the supernatant was discarded. The pellet was resuspended in 1 ml of sterile distilled water, vortexed, spun for 1 minute and the supernatant discarded. The process was repeated once. The final pellet was resuspended in 1 ml of sterile distilled water and, while continuing vortexing, 50 µl aliquots (for 4-8 bombardments) were transferred to microtubes. These aliquots were stored at 4° C. until needed.

Preparation of DNA-gold mixture and bombardment were carried out in a Class II biosafety cabinet. Six microliter of DNA (3 µl per plasmid) (1 µg/1 µl), 50 µl of $CaCl_2$ (2.5 M) and 20 µl spermidine (0.1 M, free base form, molecular biology grade) were added one by one to the 50 µl gold particles suspension. To obtain equal coating, the addition of spermidine was carried out while the mixture was still mixing. The mixture was vortexed for 3 minutes and spun for 10 second at 10,000 rpm and the supernatant discarded. The pellet was washed with 250 µl of absolute ethanol. The final pellet was resuspended in 60 µl of absolute ethanol. An aliquot (6 µl) was loaded onto the centre of the macrocarrier and air-dried.

For all three types of embryogenic calli culture, approximately 0.5-0.7 g in weight was bombarded with gold particles coated with pAHC20 and pAHC27 plasmid DNA (Christiensen and Quail, 1996), at 16-20 hours after subculturing into fresh medium. The pAHC20 plasmid carries the bar gene driven by the maize polyubiquitin promoter, first exon and first intron (Ubi1) and the NOS terminator. The pAHC27 is similar to pAHC20, except the gene is gusA. GusA is a plant reporter gene and the bar gene is a plant selectable marker gene that confers resistance to phosphinothricin (PPT). Bombardments were carried out once at the following conditions: 1100 psi rupture disc pressure: 6 mm rupture disc to macrocarrier distance; 1 mm macrocarrier to stopping plate distance, 75 mm stopping plate to target tissue distance and 67.5 mm Hg vacuum pressure. One negative control was also incorporated, i.e. embryogenic calli were bombarded with gold particles but without DNA. The bombarded tissues were then incubated at 28° C. on selection free medium in the dark until selection was initiated.

(iii) GUS Histochemical Assay

GUS assay buffer (0.1 M $NaPO_4$ buffer, pH 7.0, 0.5 mM K-Ferricyanide, 0.5 mM K-Ferrocyanide, 0.01 M EDTA, 1 mg/ml 5-Bromo-4-Chloro-3-Indolyl-β-D-glucuronide acid (dissolved in Dimethyl Formamide at 50 mg/ml) and 1 µl/ml Triton X-100) (Klein et al., 1988)+20% v/v methanol was filter-sterilized and stored at −20° C. in the dark. Two days after bombardment, the tissues were stained overnight (20 hr) with GUS buffer at 37° C., and blue spots (irrespective of its size) were scored optically using a Nikon SMZ-U stereoscopic zoom microscope and photographed with the Nikon UFX-DX system.

Figure 1B:
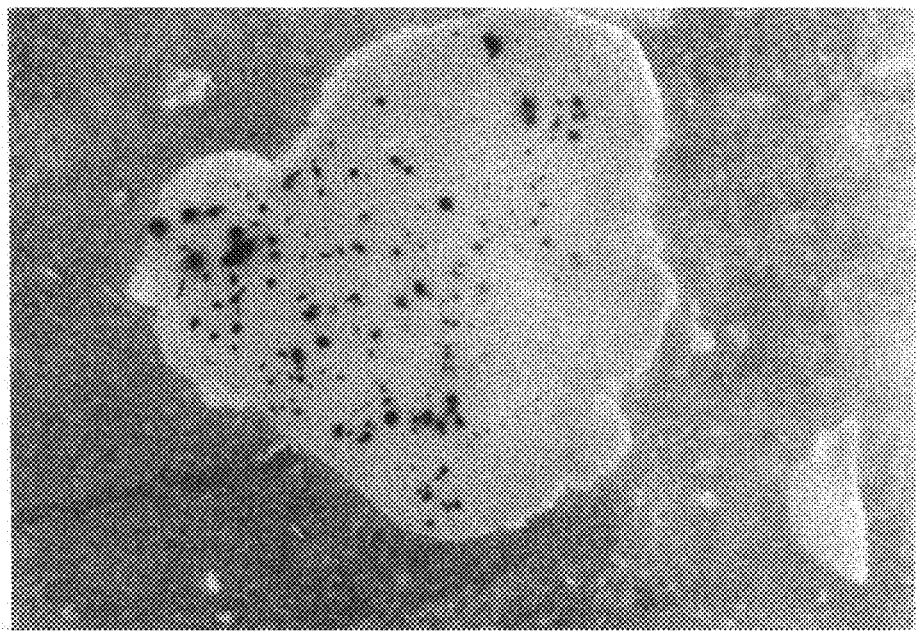

Bombardment data show that the Biolistic PDS-1000/He apparatus was capable of delivering DNA into oil palm embryogenic calli. Bombardment of the microcarrier without DNA and unbombarded tissue did not show transient GUS gene expression (FIG. 1A). DNA delivery was monitored using transient GUS expression as an indicator (FIG. 1B). Each blue spot arising from the histochemical localization of GUS activity, whether in a single cell or a group of cells, was considered as one expression unit. After histochemical staining, patches of light blue background were observed in the bombarded tissues, in addition to GUS-positive expression units (discrete blue spots). This was also observed in negative controls (tissues bombarded without DNA and non-bombarded tissues). This light blue background was successfully overcome after adding 20% methanol in GUS buffer.

(iv) Selection on Solid Medium

Selection was carried out using Basta (registered trademark) (13.5% PPT) at single concentrations of 40 ppm, 80 ppm or by gradually increasing the concentrations from 10 ppm to 20 ppm and finally to 40 ppm at 3 weeks post-bombardment. Selection was carried out at 28° C. in the dark and bombarded embryogenic calli, from solid and liquid suspension medium, were subcultured into fresh media containing the same or an increased concentration of selection agent every 4 weeks.

Figure 2:
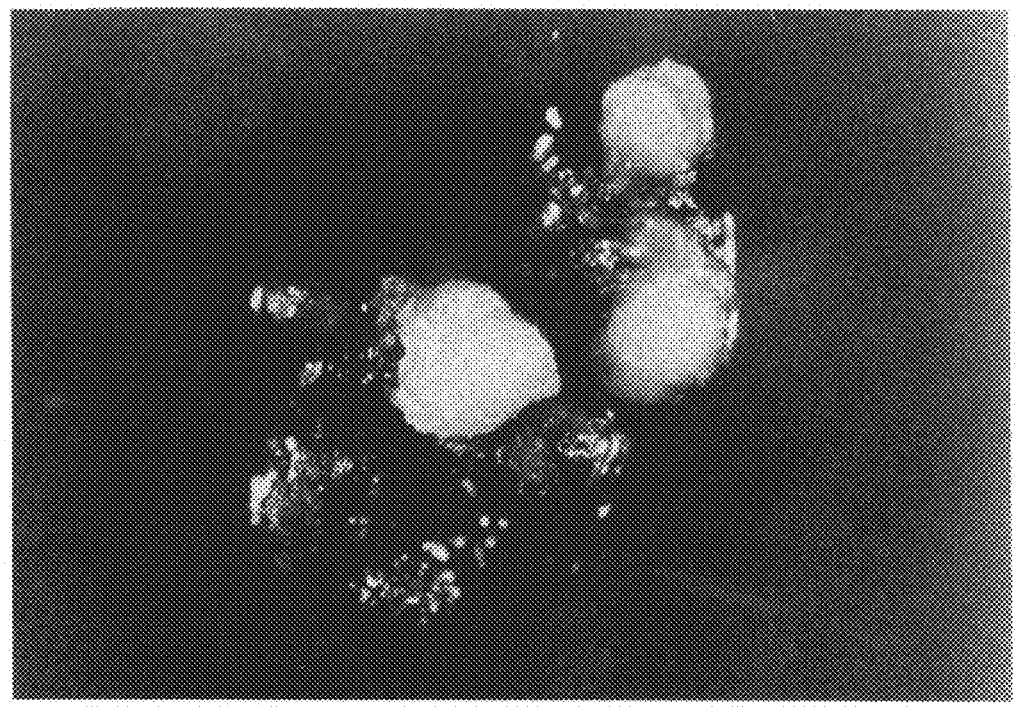
FIG. 2 is a photographic representation showing the emergence and proliferation of resistant embryogenic calli on medium containing Basta (registered trademark). Dark brown areas represent calli which did not survive selection.

Upon transfer to medium containing selection agents, untransformed embryogenic calli began to die and only resistant embryogenic calli proliferated. Resistant embryogenic calli began to emerge, surrounded by dark-brown dead embryogenic calli, at 6-8 weeks after exposure to the selection agent (FIG. 2). Due to the distinct color of transformed and untransformed embryogenic calli, selection was able to be very conveniently carried out. Resistant embryogenic calli were produced from all the above calli types and selection approaches. The resistant embryogenic calli were further subcultured in media containing selective agent for proliferation and regeneration.

(v) Selection in Liquid Medium

Selection was carried out using Basta (registered trademark) (13.5% PPT) at single concentrations of 40 ppm, 80 ppm or by gradually increasing the concentrations from 10 ppm to 20 ppm and finally to 40 ppm at 3 weeks post-bombardment. Selection was carried out at 28° C.-30° C. in the dark and bombarded embryogenic calli from the liquid suspension medium were subcultured into fresh liquid suspension medium containing the same or an increased concentration of selection agent every 4 weeks.

Upon transfer to liquid suspension medium containing selection agents, untransformed suspension embryogenic calli began to die and only resistant suspension embryogenic calli proliferated. Resistant suspension embryogenic calli began to emerge, surrounded by dark-brown dead suspension embryogenic calli, at 6-8 weeks after exposure to the selection agent. Due to the distinct color of transformed and untransformed suspension embryogenic calli, selection was able to be very conveniently carried out. Resistant suspension embryogenic calli were produced from all the above calli types and selection approaches. The resistant suspension embryogenic calli were further subcultured in liquid suspension medium containing selective agent for maturation. Regeneration of the transformed suspension embryogenic calli were carried out on solid medium as described below.

(vi) Regeneration

Figure 3:
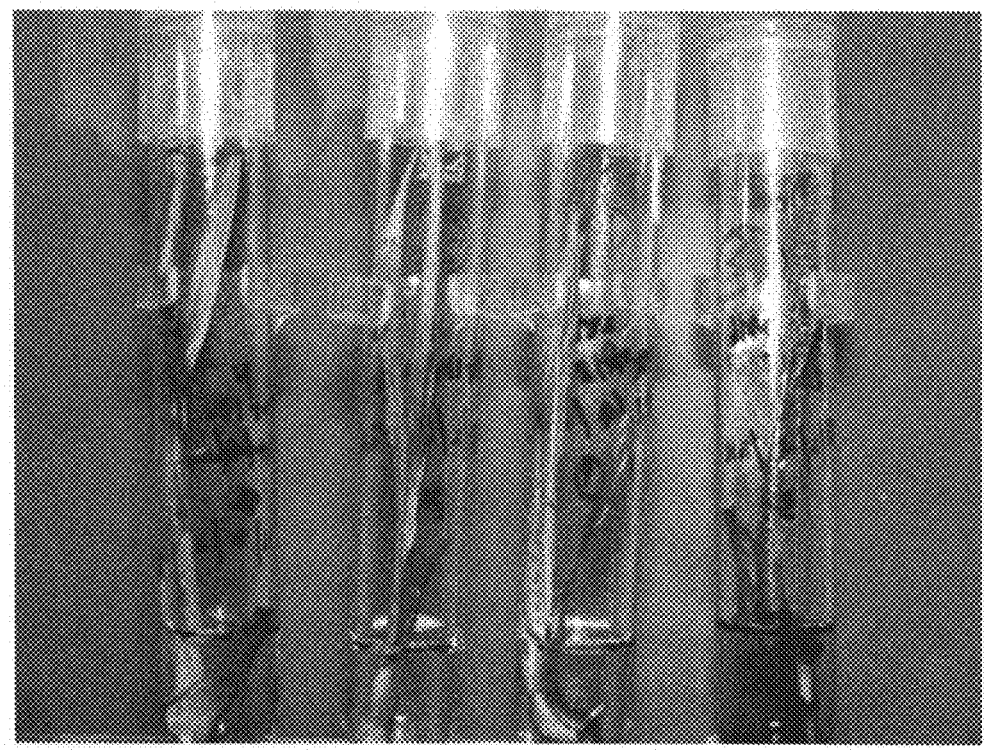
FIG. 3 is a photographic representation showing elongation and root initiation (two tubes on the right hand side) of plantlets derived from TREC cells of oil palm.

Using all the combinations of embryogenic calli types and selection approaches, it was found that only one combination was successful for proliferating the transformed embryogenic calli into polyembryogenic calli and into regenerated rooted transgenic plantlets (Table 2) (FIG. 3). This type was designated TREC (transformable and regenerable embryogenic calli). The gradually increasing (GI), step-by-step selection process was the only approach that resulted in proliferation and regeneration of transgenic embryogenic calli (Table 2). The three types of embryogenic calli are Type I (yellowish in colour, rough surface and physically friable), Type II or later known as TREC (pearl yellow in colour, smooth surface and physically solid) and Type III (light yellow to white in colour, quite smooth surface and physically solid).

TABLE 2

| Treatment | TEC/ Plate | PCR +/tested | Southern +/tested | TPEC/ Plate | TP/ Plate | PCR +/tested | Southern +/tested | TLC +/tested |
|---|---|---|---|---|---|---|---|---|
| Type I-40 | 6 | 2/2 | 2/2 | 0 | | | | |
| Type I-80 | 4 | 2/2 | 2/2 | 0 | | | | |
| Type I-GI | 7 | 2/2 | 2/2 | 0 | | | | |
| Type II-40 | 6 | 2/2 | 2/2 | 4 | 0 | | | |
| Type II-80 | 5 | 2/2 | 2/2 | 3 | 0 | | | |
| Type II-GI | 8 | 2/2 | 2/2 | 5 | 3 | 3/3 | 3/3 | 3/3 |
| Type III-40 | 7 | 2/2 | 2/2 | 5 | 0 | | | |
| Type III-80 | 6 | 2/2 | 2/2 | 3 | 0 | | | |
| Type III-GI | 7 | 2/2 | 2/2 | 4 | 0 | | | |
| TWD-40 | 0 | | | | | | | |
| TWD-80 | 0 | | | | | | | |
| TWD-GI | 0 | | | | | | | |

TEC/Plate Number of transformed embryogenic calli obtained from a single bombarded plate (mean of three plates)
TPEC/Plate Number of transformed polyembryogenic calli per bombarded plate
TP/Plate Number of transgenic plant lines produced per bombarded plate
+/tested Number of samples showing positive results (PCR/Southern/TLC) over total number of samples tested
Type I-40 Type I embryogenic calli selected on 40 ppm Basta (registered trademark), and so on
TWD Embryogenic calli bombarded using gold particle but without DNA
GI Gradually increasing When a number 0 was obtained, no further analysis was carried out, as there was no sample available.

TREC cells were available only for a short duration, 2-3 weeks, before these changed into Type III calli, which was undesirable. It was very important to isolate the TREC cells at the right time and use them for transformation. Type I failed to produced any transgenic polyembryogenic calli. However, Types II and III were successful in producing transgenic polyembryogenic calli. Only for Type II, though, were whole plants able to be regenerated from the transgenic polyembryogenic calli. The transformed embryogenic calli from Type I and III, from which transgenic plants were not able to be regenerated, actually looked alive, as they didn't turned brown on medium containing Basta (registered trademark).

At this stage, PCR and Southern blot hybridization analyses were carried out to ensure that the Basta (registered trademark)-resistant embryogenic calli were actually transformed and were not escapes. PCR and Southern analyses revealed positive results, indicating that they were indeed transformed. The results indicated that Type I and III embryogenic calli were transformable but not regenerable. Only Type II or TREC cells were capable of both receiving foreign genes and further regenerate into transgenic plants. By comparison, in single concentrations of selection agent, either 40 or 80 ppm, transgenic embryogenic calli were produced but all forms of these cells failed to proliferate further and regenerate. By gradually increasing the concentration of selection agent, transgenic embryogenic calli were produced which were able to further proliferate into polyembryogenic calli capable of being regenerated to transgenic plants.

Figure 4A:
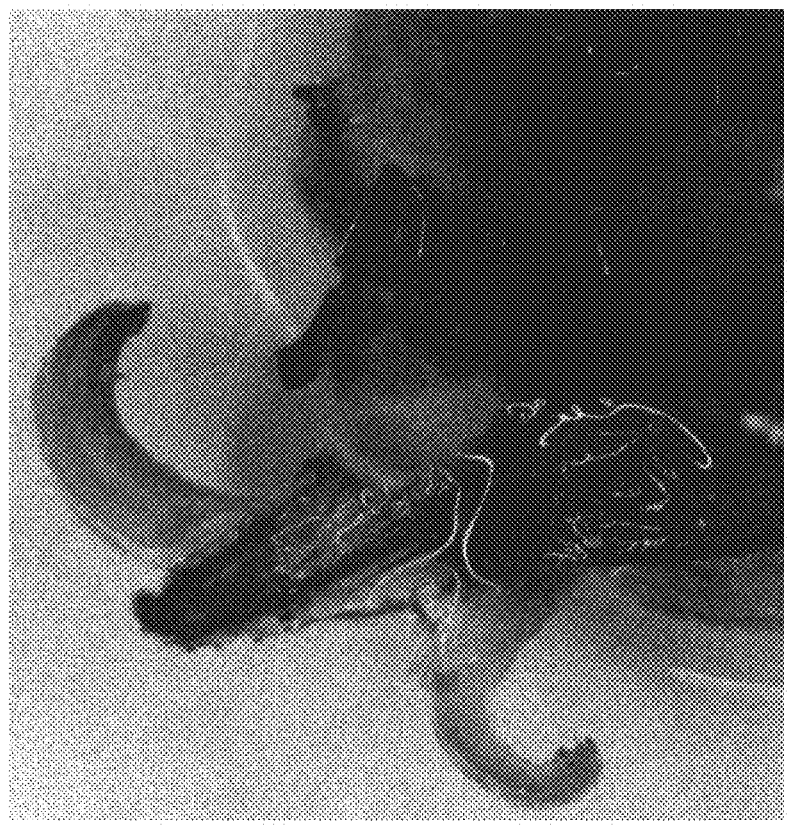
FIGS. 4A, 4B and 4C are photographic representations showing gusA gene expression (GUS histochemical assay) on leaves of newly-regenerated oil palm. 4A: A few leaves from one transgenic plant; 4B: one leaf from a transgenic plant, and 4C: young leaves from control (non-transformed) oil palm plant.
Figure 4B:
Figure 4C:
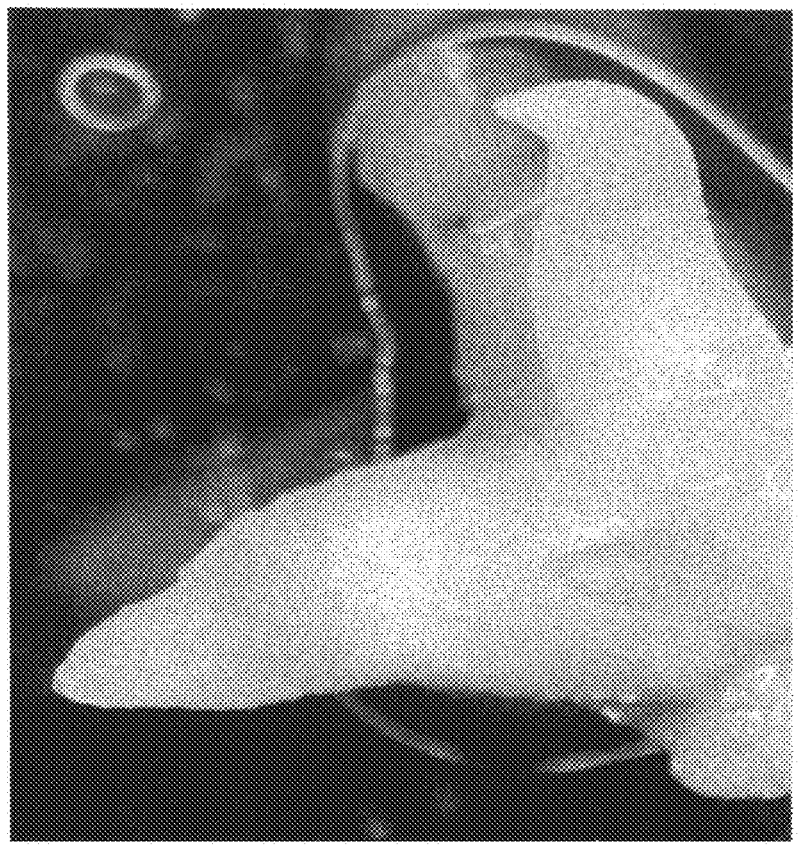

Some leaves of the newly-regenerated transgenic oil palm plants were subjected to GUS histochemical assay, as described in Example 4 (iii), to examine the expression of one of the transgenes. Leaves from transgenic plants stained dark blue, indicating expression of the GUS gene, whereas the control leaves remained white in colour (FIG. 4). This showed that the transgenic plants expressed the transgene used.

Figure 5A:
FIGS. 5A, 5B and 5C are photographic representations showing fully-grown transgenic oil palm derived from transformed TREC cells of oil palm plants. The plants exhibit normal phenotypes, even after a few years in polybags in the nursery. 5A: Transgenic oil palm plants aged 8 months; 5B: transgenic oil palm plants aged 18 months, and 5C: transgenic oil palm plants aged 36 months. Note: For size a 12 inches ruler included.
Figure 5B:
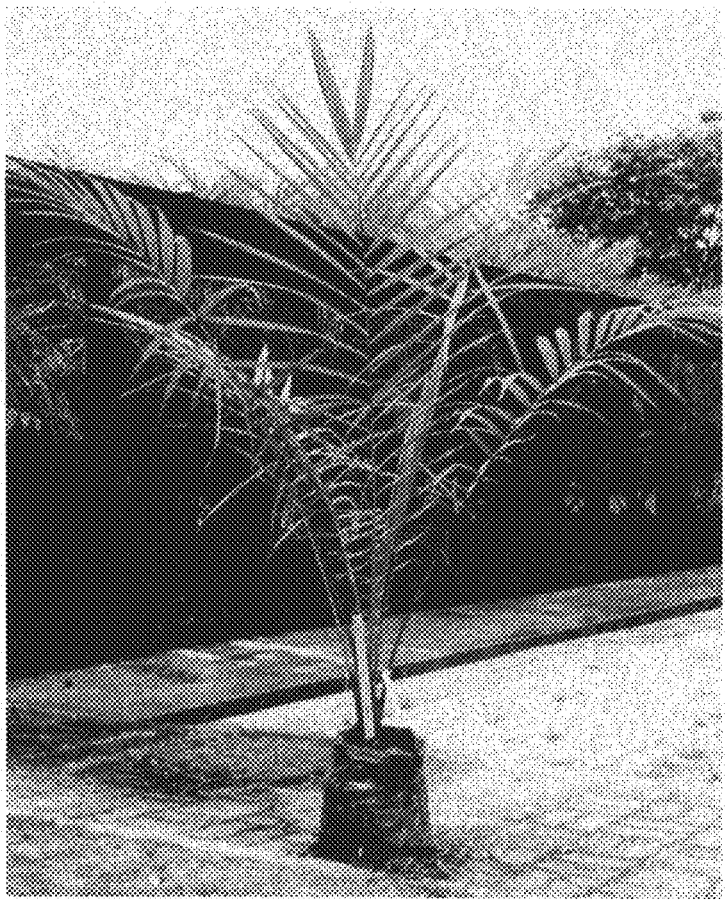
Figure 5C:
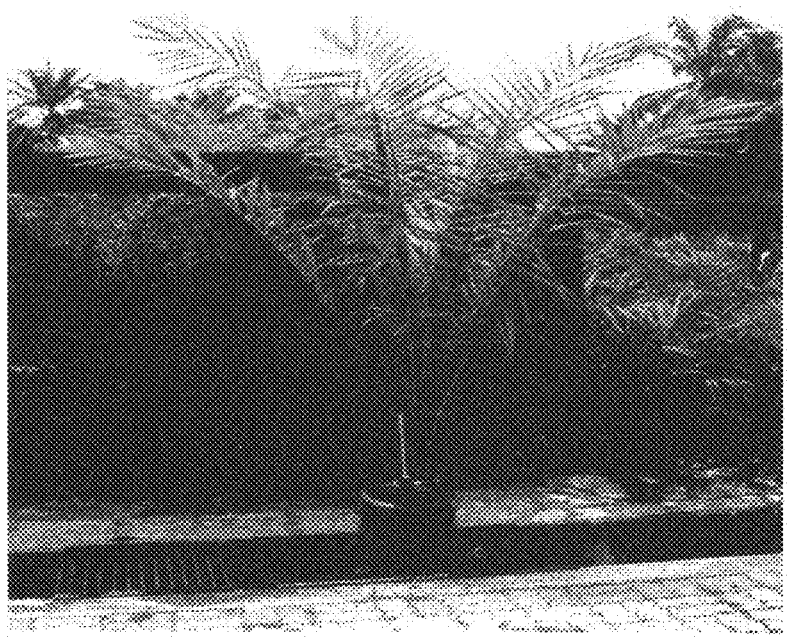

Transgenic plants, obtained from TREC cells selected by gradually increasing the concentration of selection agent have produced enough roots and shoots to permit transfer to the nursery in polybags containing soil. The plants exhibited normal phenotypes, even after a few years in polybags (FIG. 5). Molecular and protein analyses have been performed to verify the transgenic status of the plants regenerated (see Example 5, below).

Example 5

Analyses of Regenerated Plants (i) Preparation of Total DNA from Regenerated Plants Genomic DNA was isolated from leaves of the transgenic plants and one untransformed plant as a negative control. Total DNA was isolated using the method by Ellis (1993). Leaf pieces (0.5-1.0 g) were placed in a mortar and liquid nitrogen added. The frozen leaves was ground with a pestle and 8 ml EB2 buffer (500 mM NaCl, 100 mM Tris-Cl, pH 8.0 and 50 mM EDTA, pH 8.0) was added. After a little more grinding, 400 µl 20% w/v SDS was added and the mixture ground again. Eight milliliter of phenol mix (1:1; phenol: chlorofom) was added, mixed by several inversions and centrifuged (12,000 rpm, 5 min, RT). The aqueous phase was transferred into a new centrifuge tube and mixed with 16 ml of absolute ethanol. DNA was removed by centrifugation (12,000 rpm, 15 min, RT). The pellet was washed with 70% ethanol and dissolved in 300 µl TE (10 mM Tris-Cl and 1 mM EDTA, pH 8.0).

(ii) Polymerase Chain Reaction (PCR) Analysis

The following primers were used to amplify the bar gene and part of the ubiquitin promoter:

BARF1    5' GGTC TGCACCATCGTCAACC 3'    SEQ ID NO: 1
and
BARR1    5' ACTCACCGCGACGTCTGTCG 3'    SEQ ID NO: 2 resulting in a band sized 1550 bp. Amplification of the bar gene was carried out using a touch-down PCR procedure. PCR reactions were carried out in the following mixture: DNA (50 ng total DNA or 5 ng plasmid DNA)+reaction buffer (containing 50 mM KCl and 10 mM Tris-Cl pH 8.3)+ dNTPs (200 µM each)+1.5 mM MgCl$_2$+primers and taq DNA polymerase. The touch down procedure is as follow: hot start at 95° C. (300 sec), denature at 94° C. (45 sec), anneal at 70°

C. (45 sec; −0.5° C. per cycle for 10 cycle) and elongate at 72° C. (60 sec) followed by 24 cycle of 94° C. (45 sec), 65° C. (45 sec) and 72° C. (60 sec) and finally 72° C. for 120 sec. Amplified DNA fragments were checked by running 1.4% agarose gel electrophoresis in 1×TBE buffer.

Genomic DNA was isolated from leaves of the transgenic regenerated plants and one untransformed plant as a negative control. DNA from all transformed plants and one untransformed plant was subjected to amplification of an oil palm internal control sequence for reliable PCR analysis of the transgene. Since all the plants were derived from embryogenic callus bombarded with pAHC20 (a plasmid carrying bar gene under the control of Ubiquitin 1 promoter) (Christiensen and Quail, 1996) and selected on Basta (registered trademark), the amplification of the bar gene was used for verification of transformation. After amplification using a touch-down protocol, all the transformants, and the positive controls showed amplification of the bar gene. No bands were amplified from untransformed control tissue. PCR analysis demonstrated that all the regenerated plants from the Basta (registered trademark)-resistant TREC cells contained the bar gene used for selection. The expected band (1550 bp) was amplified for all the TREC-derived plants. This result is consistent with the stable integration of the transgene into these regenerated oil palm plants. Since amplification of transgenes using PCR is not definitive evidence of stable integration of transgenes into a host genome, Southern blot hybridization analysis, with positive signals on high molecular weight DNA hybrids between the transgene and host genomic DNA, was also required. Refer to next section.

(iii) Southern Blot Hybridization Analysis

Digested DNA from 0.8% agarose gel in 1×TBE buffer was capillary transferred onto nylon membrane by the method of Southern (1975). Agarose gel containing 10 μg of the BamHI-digested DNA was soaked in depurinating buffer (0.2 M HCl) for 10 minutes, denaturing buffer (1.5 M NaCl and 0.5 M NaOH) for 45 minutes and transferred into neutralization buffer (1 M Tris pH 8.0 and 1.5 M NaCl) for 1 hour. The gel was later transferred onto 3MM paper with the end of the paper soaked into 20×SSC (175.3 g NaCl and 88.2 g sodium citrate, adjusted pH to 7.0 with 10 M NaOH). Nylon membrane (Amersham) was placed on top of the gel followed by 2 sheets of 3MM paper, paper towels, a glass plate and a 500 g weight. The set-up was left overnight (16-20 hours) to allow all the DNA to be transferred onto the membrane. After transfer, the membrane was washed with 2×SSC and baked at 80° C. for 2-4 hours.

Oligolabelling of the bar gene fragment (prepared by PCR) for use as probe was carried out using the method by Feinberg and Vogelstein (1983). DNA (6 μl; ~10 ng) was added to 20 μl 5×OLB (0.25 M Tris-HCl pH 8.0, 25 mM $MgCl_2$ 0.36% v/v 2-mercaptoethanol, 1 M hepes pH 6.6, 30% hexadeoxyribonucleotides (90 O.D. units/ml)), boiled for 5 minutes and chilled on ice. The following was added to the above mixture: 2 μl 0.1M dNTPs (except dCTP), 5 μl $\alpha^{32}P$(dCTP) 370 KBq/μl), 2 μl 10 mg/ml BSA, 1 μl Klenow (6 U/μl) and 14 μl 1M distilled water. The labelling reaction was carried out by incubating at 37° C. for 30 minutes. Probe was denatured by the addition of 50 μM NaOH for 1 minute, 50 μl 1 M HCl for 1 minute and 50 μl Tris-HCl (pH 7.5) for 1 minute. The denatured probe was stored on ice until use.

Pre-hybridization and hybridization were carried out using the same buffer. Membrane, transferred with DNA, was prehybridized (40% pipes/NaCl pH 6.8 (1.5% pipes, 8.7% NaCl and 0.37% EDTA [pH 8.0]); 20% Denhardts 50× [1% BSA, 1% Ficoll, 1% PVP and 10% SDS]; 0.5% SS-DNA 10 mg/ml) and 39.5% distilled water) for 90 minutes at 65° C. Denatured DNA probe was added and hybridized for 20 hours at 65° C. After hybridization, the membrane was prewashed once with 2×SSC for 1 minute and washed twice in 0.1×SSC and 0.1% w/v SDS. The first wash was carried out for 30 minutes and the second one for 45 minutes, both at 65° C. The washed membrane was wrapped with saran wrap and exposed to X-ray film with an intensifying screen at −70° C.

Figure 6:
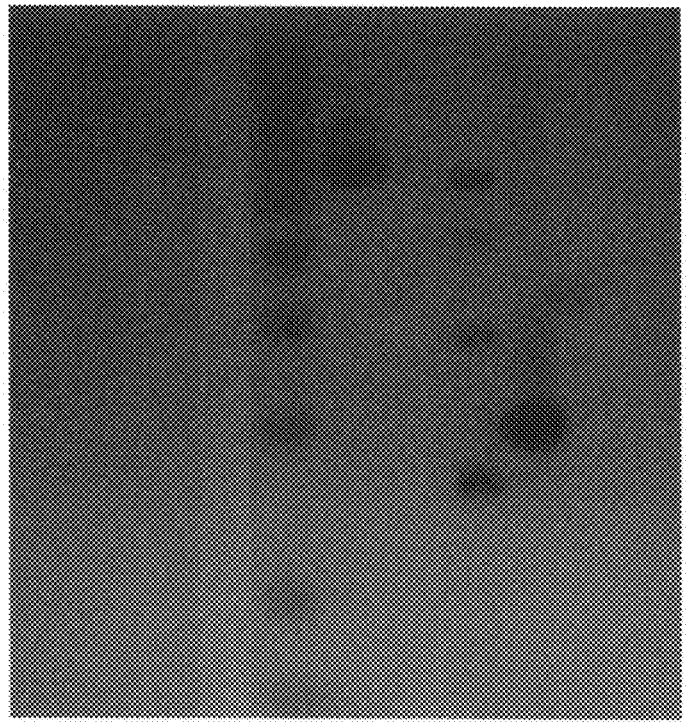
FIG. 6 is a photographic representation showing Southern blot hybridization of transgenic oil palm plants. Lanes 1-5 contain BamHI-digested DNA of transgenic regenerants and Lane U contains untransformed control. Radiolabelled-bar gene was used as probe. Hybridization was detected in all transgenic plants; no hybridization was detected in the untransformed control. Lane M=1 Kb DNA marker (BRL).

Hybridization was carried out on undigested DNA isolated from five regenerated plants derived from different resistant embryogenic callus clumps, and from one untransformed control plant. A PCR-amplified bar gene was used as a probe for the hybridization. Hybridization to undigested high molecular weight DNA was observed with all five regenerants and with the positive control. No hybridization to the untransformed control was observed. Hybridization to the high molecular weight DNA indicated that stable integration of the transgene into the genome of regenerated oil palm plants had occurred. Hybridization to BamHI digested DNA using the same probe again showed integration of the transgene into the oil palm genome (FIG. 6). No hybridization to the untransformed DNA was observed. Hybridization with BamHI digestion is expected to reveal bands at least 600 bp, which is the size of the bar gene. In this figure, multiple and single bands can be observed all of which were larger than 600 bp. Bands that are larger than the bar gene fragment (600 bp) indicate integration of the transgene into the oil palm genome. The larger bands are expected to contain both the introduced plasmid as well as oil palm genomic DNA. DNA from all transgenic plant lines hybridized to these unique bands as a result of independent transformation events. Single as well as multiple insertion was also observed.

(iv) Phosphinothricin Acetyltransferase (PAT) Analysis

Southern analysis confirmed integration of the transgene. Protein (enzymatic) assay, to prove that the introduced gene is functional, was then carried out. The presence of an active bar gene was confirmed by determining the product of the gene, an enzyme called phosphinothricin acetyltransferase (PAT). The enzyme inactivates phosphinothricin (the active ingredient of the herbicide Basta (registered trademark)) by acetylation.

PAT assay was carried out using the method by DeBlock et al., 1987. About 100 mg of leaf tissue from transgenic plants and from non-transformed plants was homogenized in a buffer composed of: 50 mM Tris-HCl, pH 7.5; 2 mM EDTA; 0.1 mg/ml leupeptin; 0.3 mg/ml bovine serum albumin (BSA); 0.3 mg/ml Dl-Dithiothreitol (DTT) and 0.15 mg/ml phenylmethylsulfonyl fluoride (PMSF).

After subsequent centrifugation, 12.5 μl of clear supernatant was incubated with 0.75 μl of 1 mM PPT (Sigma, USA) and 1.25 μl of $^{14}C$ acetyl-CoenzymeA (57 mCi/mmol) (Amersham, UK) at 37° C., for 30 minutes. Six μl of the reaction was transferred to a thin-layer chromatography plate in a mixture of isopropanol:ammonium solution (3:2 parts by volume). Separated PPT and acetyl-PPT were detected by autoradiography.

Figure 7:
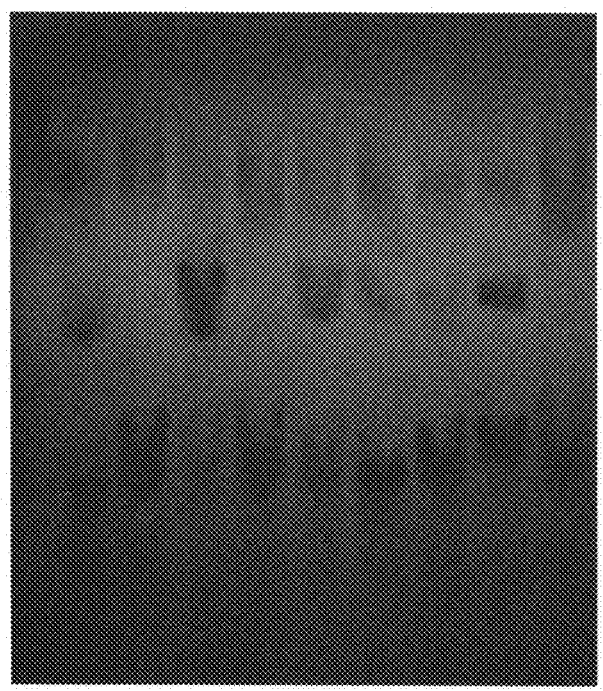
FIG. 7 is a photographic representation showing thin layer chromatography of PAT activity in Basta (registered trademark)-resistant transgenic oil palm plants. Lane U: protein from untransformed control; lane T: protein from transgenic embryogenic callus (positive control); lanes 1-7: proteins from transgenic plants. Arrow indicates acetylated protein band.

Protein isolated from Basta (registered trademark)-resistant transgenic plants demonstrated PAT activity, based on thin layer chromatography analysis (FIG. 7). The protein isolated from untransformed plant failed to show any PAT activity.

(v) Analysis of Herbicide Resistance

Another approach to test for Basta (registered trademark) resistance in transgenic oil palm plants is by direct painting of leaves with a solution of herbicide. Leaves from 3-year-old transgenic oil palm plants were painted with either 0.015% v/v (half strength) or 0.03% v/v Basta (registered trademark) solutions containing 0.1% v/v Tween 20 and 0.1% v/Triton X-100 (Modified from Castillo et al., 1993). Symptoms were evaluated 2 weeks after application. The 0.015% v/v and 0.03% v/v Basta (registered trademark) solutions were applied to approximately two-thirds of each leaf; leaves of both control plants and Basta (registered trademark)-resistant transgenic oil palm plants were analyzed.

The leaves from control palms became brown and wilted after 2 weeks, compared with the transgenic plants which remained healthy and green (FIG. 8). These results showed that the transgenic plants were resistant to Basta (registered trademark) and that the transgene was stably expressed, even after 3 years.

Example 6

GUS Gene Expression in Callus Derived from Transgenic Oil Palm Plantlets

These perennial oil palm plants produce pollen and embryos in their fruits 3-5 years after planting in soil. Analyzes of the GUS histochemical assay or PAT assay for both of the transgenes in the pollen and embryos of the oil palm is essential to test for fertility and transgene inheritance to progeny, respectively. As the time required is very long, an alternative approach was employed in order to see the stability of the transgene in this long-regeneration crop.

Calli were developed from Basta (registered trademark)-resistant oil palm plantlets and were subjected to GUS histochemical assay. Calli were initiated from the transgenic Basta (registered trademark)-resistant oil palm plantlets and also from non-transformed oil palm plantlets, as described in Example 2. The calli obtained were subjected to GUS histochemical assay, as described in Example 4.

Figure 9B:
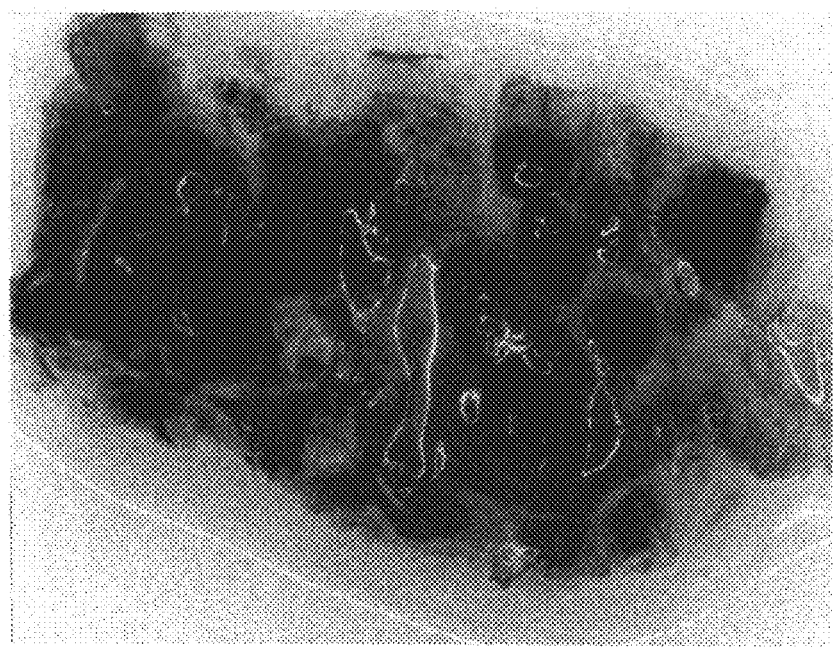
FIGS. 9A, 9B and 9C are photographic representations showing gusA gene expression (GUS histochemical assay) on callus derived from leaves of newly-regenerated oil palm. 9A: Callus derived from leaves of transgenic oil palm plant; 9B: callus derived from leaves of transgenic oil palm plant, and 9C: callus derived from leaves of control (non-transformed) oil palm plant.
Figure 9A:
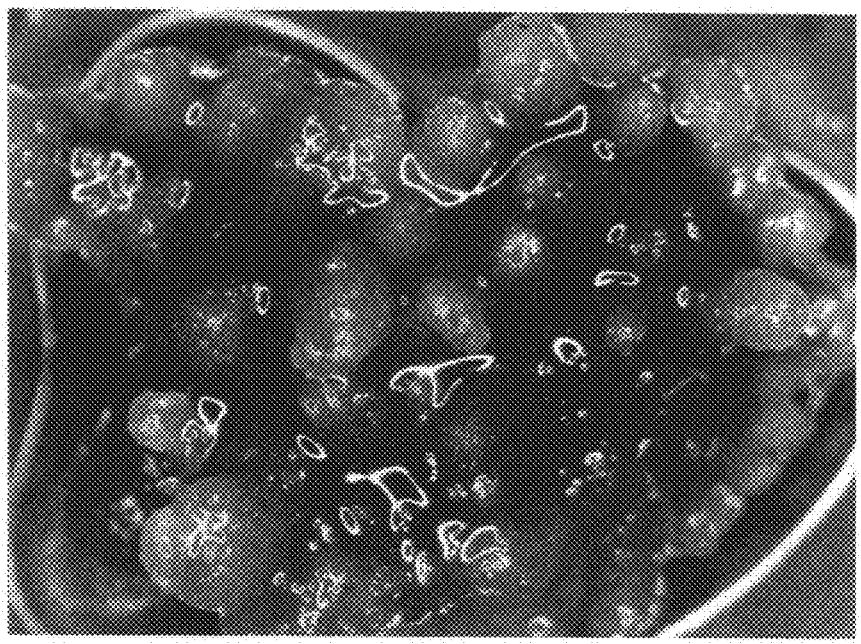
Figure 9C:
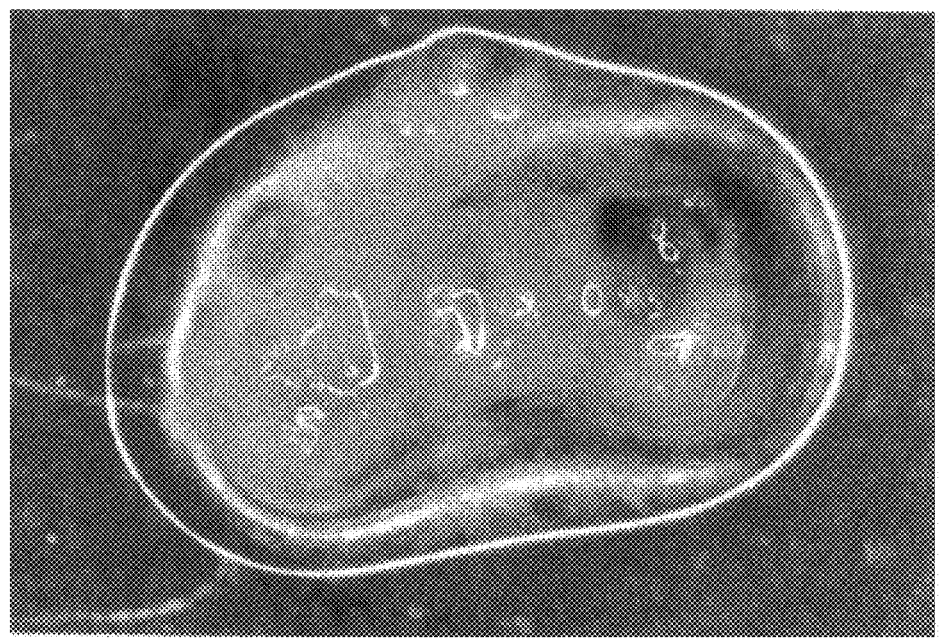

After GUS histochemical staining (20 hours), callus derived from the transgenic Basta (registered trademark)-resistant oil palm plantlets turned blue as shown in FIG. 9A. No GUS gene expression was observed in the callus derived from non-transformed oil palm plantlets (FIG. 9B). This shows that the transgenic Basta (registered trademark)-resistant oil palm plantlets are capable of expressing the GUS gene at a long duration and in undifferentiated form.

Example 7

Regeneration of Transgenic Plants from Types I and III Embryogenic Calli

The following modifications and alternative methods result in the ability to regenerate transgenic plants from transformed Types I and III embryogenic calli.

The regeneration medium is modified by, inter alia, adding or changing the concentration and types of some hormones or vitamins; changing the temperature; changing the light intensity and/or duration; changing the pH and other components and conditions of the growth.

Alternatively, one or more of the following physical treatments are used to change Types I and III embryogenic calli into Type II (TREC), and finally produce transgenic plants: cutting the Types I and III embryogenic calli into small pieces; heating or osmotic treatment; exposure to darkness for a particular duration.

Example 8

DNA Delivery into and Selection of Transformed Primary Calli

As well as transforming embryogenic calli, primary calli were also tested as target tissue for transformation. Resistant calli were successfully obtained from the bombarded calli. However, the calli failed to further proliferate into embryogenic calli cells (Table 3).

TABLE 3

| Treatment | TC/Plate | PCR +/tested | Southern +/tested | TEC/Plate | TP/Plate | PCR +/tested | Southern +/tested | TLC +/tested |
| --- | --- | --- | --- | --- | --- | --- | --- | --- |
| Callus-40 | 7 | 20/20 | 20/20 | 0 | | | | |
| Callus-80 | 5 | 20/20 | 20/20 | 0 | | | | |
| Callus-GI | 7 | 20/20 | 20/20 | 0 | | | | |
| TWD-40 | 0 | | | | | | | |
| TWD-80 | 0 | | | | | | | |
| TWD-GI | 0 | | | | | | | |

TC/Plate Number of transformed calli per bombarded plate
TEC/Plate Number of transformed embryogenic calli obtained from a single bombarded plate (mean of twenty plates)
TP/Plate Number of transgenic plant lines produced per bombarded plate
+/tested Number of samples showing positive results (PCR/Southern/TLC) over total number of samples tested
Callus-40 Primary calli selected on 40 ppm Basta (registered trademark), and so on
TWD Primary calli bombarded using gold particle but without DNA
GI Gradually increasing Example 9

Regeneration of Transgenic Plants from Transformed Primary Calli and Immature Embryos The following alternative method results in the production of transgenic plants from the target primary callus tissue and from immature embryos.

Bombarded calli are proliferated to produce embryogenic calli, without selection. The resulting embryogenic calli from the bombarded calli are used to select TREC type II embryogenic calli and the TREC calli are subsequently used for selection and regeneration of transgenic plants.

Similarly, immature embryos are used as a target tissue for transformation. Bombarded immature embryos are used for callus initiation and proliferation to produce embryogenic calli, without selection. The resulting embryogenic calli from the bombarded immature embryos are used to select TREC type II embryogenic calli and the TREC calli are then used for selection and regeneration of transgenic plants.

Transformed Types I and III embryogenic calli derived from callus or immature embryos target tissue and produced as described in Example 7, above, are also used to produce transgenic plants as described in this Example 9.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for transforming cells of an oil palm plant with genetic material comprising:
   (i) obtaining an explant from an oil palm plant;
   (ii) culturing said explant in callus-induction medium to generate three morphological types of embryogenic calli: Type I, Type II, and Type III;
   (iii) isolating a transformable and regenerable Type II embryogenic callus (TREC) therefrom through culturing in a 2,4-D-containing callus-induction medium supplemented with thiamine or coconut water;
   (iv) transforming said transformable and regenerable Type II embryogenic callus with genetic material comprising a selectable marker to provide transformed embryogenic calli; and
   (v) selecting the transformed embryogenic calli by gradually increasing the concentration of a selection agent.

2. The method according to claim 1, wherein the explant is obtained from a root of an oil palm plant.

3. The method according to claim 1, wherein the explant is obtained from a leaf of an oil palm plant.

4. The method according to claim 1, wherein the explant is obtained from inflorescences of an oil palm plant.

5. The method according to claim 4, wherein the inflorescences are both in male and female form.

6. The method according to claim 1, wherein the explant is obtained from an immature embryo of an oil palm plant.

7. The method according to claim 6, wherein the immature embryos are from fruits of the oil palm plant 5 to 18 weeks after anthesis.

8. The method according to claim 1, wherein the concentration of thiamine is 0.5 g/l.

9. The method according to claim 1, wherein the concentration of coconut water is 100 ml/l.

10. The method according to claim 1, wherein the embryogenic callus is subsequently transformed.

11. The method according to claim 10, wherein the embryogenic callus are from both solid and liquid suspension medium.

12. The method according to claim 10, wherein the embryogenic callus are of two sizes, wherein the first size is less than 1.0 mm and the second size is between 1.0 mm and 3.0 mm.

13. The method according to claim 10, wherein transformation is carried out by microprojectile bombardment.

14. The method according to claim 13 wherein transformation is carried out by co-bombardment of more then 1 plasmids.

15. The method according to claim 13, wherein transformation is carried out by co-bombardment with 2 plasmids.

16. The method according to claim 10, wherein transformation is carried out by *Agrobacterium*-mediated infection.

17. The method according to claim 10, wherein the embryogenic callus are subcultured onto fresh solid medium and transformed 16 to 24 hours after subculturing onto the fresh solid medium.

18. The method according to claim 1, wherein the selection is carried out on a solid medium containing a gradually increasing concentration of the selection agent, wherein the concentration of the selection agent ranges from 10 mg/l to 40 mg/l.

19. The method according to claim 1, wherein the selection is carried out in liquid medium containing a gradually increasing concentration of the selection agent, wherein the concentration of the selection agent ranges from 10 mg/l to 40 mg/l.

20. The method according to claim 1, wherein the selection is carried out on a solid medium containing 40 mg/l of selection agent.

21. The method according to claim 1, wherein the selection is carried out in liquid medium containing 40 mg/l of selection agent.

22. The method according to claim 1, wherein the selection is carried out on a solid medium containing 80 mg/l of selection agent.

23. The method according to claim 1, wherein the selection is carried out in liquid medium containing 80 mg/l of selection agent.

24. The method according to claim 1, wherein said genetic material confers a trait of at least one of increased yield of oil; resistance to attack by disease-causing pathogenic agents; production of modified lipids and non-lipid components of palm oil; production of improved quality palm oil; production of industrial oils or chemicals, or production of nutraceutical or pharmaceutical compounds.

25. The method of claim 1, wherein the genetic material of the genetically-modified oil palm plant encodes acetyl CoA carboxylase (ACCase), chitinase, glucanase, cry (*Bacillus thuringiensis*), β-ketoacyl ACP synthase II (KASII), ketoacyl ACP synthase I (KASI), ketoacyl ACP synthase III (KASIII), thioesterases, desaturases, fatty acid elongases, oleate hydroxylase, acyltransferases, beta-ketothiolase, threonine deaminase/dehydratase, acetoacetyl CoA reductase, or polyhydroxybutyrate synthase.

26. A method for producing a genetically-modified oil palm plant, said method comprising:
(i) obtaining an explant from an oil palm plant wherein the explant is obtained from a root, a leaf, an inflorescence, or an immature embryo of the oil palm plant;
(ii) culturing said explant in callus-induction medium to generate a Type II embryogenic callus therefrom;
(iii) transforming said embryogenic callus with genetic material to provide a transformed embryogenic callus;
(iv) selecting the transformed embryogenic calli by gradually increasing a selection agent;
(v) forming a polyembryogenic callus culture from the transformed embryogenic callus; and
(vi) regenerating transformed plantlets from said polyembryogenic callus cultures.

27. The method according to claim 26, wherein the inflorescences are both in male and female form.

28. The method according to claim 26, wherein the explant is cultured in 2,4-D-containing induction medium supplemented with thiamine or coconut water.

29. The method according to claim 28, wherein the concentration of 2,4-D is $5 \times 10^{-5}$ M.

30. The method according to claim 28, wherein the concentration of thiamine is 0.5 g/l.

31. The method according to claim 28, wherein the concentration of coconut water is 100 ml/l.

32. The method according to claim 26, wherein the polyembryogenic callus culture is formed by maintaining the transformed embryogenic callus is in a solid or liquid suspension medium comprising growth regulators.

33. The method according to claim 32, wherein said medium comprises indole-3-butyric acid.

34. The method according to claim 33, wherein the concentration of indole-3-butyric acid is 5 μM.

35. The method according to claim 26, wherein said genetic material confers a trait of at least one of increased yield of oil; resistance to attack by disease-causing pathogenic agents; production of modified lipids and non-lipid components of palm oil; production of improved quality palm oil; production of industrial oils or chemicals, or production of nutraceutical or pharmaceutical compounds.

36. The method of claim 26, wherein the genetic material of the genetically-modified oil palm plant encodes acetyl CoA carboxylase (ACCase), chitinase, glucanase, cry (*Bacillus thuringiensis*), β-ketoacyl ACP synthase II (KASII) (May be deleted), ketoacyl ACP synthase I (KASI), ketoacyl ACP synthase III (KASIII), thioesterases, desaturases, fatty acid elongases, oleate hydroxylase (May be deleted), acyltransferases, beta-ketothiolase, threonine deaminase/dehydratase, acetoacetyl CoA reductase, or polyhydroxybutyrate synthase.

37. A method for producing a genetically-modified oil palm plant comprising:
(i) obtaining an explant from an oil palm plant;
(ii) culturing said explant in callus-induction medium to generate a Type II embryogenic callus therefrom;
(iii) transforming said Type II embryogenic callus with genetic material to provide a transformed Type II embryogenic callus;
(iv) selecting the transformed Type II embryogenic callus by gradually increasing a selection agent;
(v) forming a polyembryogenic callus culture from the transformed Type II embryogenic callus; and
(vi) regenerating transformed plantlets from said polyembryogenic callus culture.

38. The method according to claim 37, wherein the explant is obtained from a root of an oil palm plant.

39. The method according to claim 37, wherein the explant is obtained from a leaf of an oil palm plant.

40. The method according to claim 37, wherein the explant is obtained from inflorescences of an oil palm plant.

41. The method according to claim 40, wherein the inflorescences are both in male and female form.

42. The method according to claim 37, wherein the explant is obtained from an immature embryo of an oil palm plant.

43. The method according to claim 37, wherein the explant is cultured in 2,4-D-containing induction medium supplemented with thiamine or coconut water.

44. The method according to claim 43, wherein the concentration of 2,4-D is $5 \times 10^{-5}$ M.

45. The method according to claim 43, wherein the concentration of thiamine is 0.5 g/l.

46. The method according to claim 43, wherein the concentration of coconut water is 100 ml/l.

47. The method according to claim 37, wherein the polyembryogenic callus culture are formed by maintaining the transformed embryogenic callus in solid or liquid suspension medium comprising growth regulators.

48. The method according to claim 47, wherein said medium comprises indole-3-butyric acid.

49. The method according to claim 47, wherein the concentration of indole-3-butyric acid is 5 μM.

50. The method according to claim 37, wherein said genetic material confers a trait of at least one of increased yield of oil; resistance to attack by disease-causing pathogenic agents; production of modified lipids and non-lipid components of palm oil; production of improved quality palm oil; production of industrial oils or chemicals, or production of nutraceutical or pharmaceutical compounds.

51. The method of claim 37, wherein the genetic material of the genetically-modified oil palm plant encodes acetyl CoA carboxylase (ACCase), chitinase, glucanase, cry (*Bacillus thuringiensis*), β-ketoacyl ACP synthase II (KASII) (May be deleted), ketoacyl ACP synthase I (KASI), ketoacyl ACP synthase III (KASIII), thioesterases, desaturases, fatty acid elongases, oleate hydroxylase (May be deleted), acyltransferases, .beta.-ketothiolase, threonine deaminase/dehydratase, acetoacetyl CoA reductase, or polyhydroxybutyrate synthase.

52. The method of claim 1, wherein the concentration of 2,4-D is $5 \times 10^{-5}$ M.

53. The method of claim 1, wherein the concentration of thiamine is 0.5 g/l.

54. The method of claim 1, wherein the concentration of coconut water is 100 ml/l.

55. The method of claim 3, wherein the concentration of 2,4-D is $5 \times 10^{-5}$ M.

56. The method of claim 25, wherein the thioesterase is palmitoyl ACP thioesterase.

57. The method of claim 36, wherein the thioesterase is palmitoyl ACP thioesterase.

58. The method of claim 51, wherein the thioesterase is palmitoyl ACP thioesterase.

59. The method of claim 25, wherein the desaturase is stearoyl ACP desaturase or oleoyl CoA desaturase.

60. The method of claim 36, wherein the desaturase is stearoyl ACP desaturase or oleoyl CoA desaturase.

61. The method of claim 51, wherein the desaturase is stearoyl ACP desaturase or oleoyl CoA desaturase.

62. The method of claim 1 wherein said isolation of Type II embryogenic callus (TREC) was conducted before said Type II calli changed to Type III.

* * * * *